(12) United States Patent
Ando et al.

(10) Patent No.: US 11,649,432 B2
(45) Date of Patent: May 16, 2023

(54) METHOD FOR PRODUCING RETINAL PIGMENT EPITHELIAL CELLS

(71) Applicants: SUMITOMO PHARMA CO., LTD., Osaka (JP); HEALIOS K.K., Tokyo (JP)

(72) Inventors: Satoshi Ando, Kobe (JP); Takao Kuroda, Kobe (JP)

(73) Assignees: SUMITOMO PHARMA CO., LTD., Osaka (JP); HEALIOS K.K., Tokyo (JP)

( * ) Notice: Subject to any disclaimer, the term of this patent is extended or adjusted under 35 U.S.C. 154(b) by 0 days.

(21) Appl. No.: 15/757,202

(22) PCT Filed: Sep. 8, 2016

(86) PCT No.: PCT/JP2016/076524
§ 371 (c)(1),
(2) Date: Mar. 2, 2018

(87) PCT Pub. No.: WO2017/043605
PCT Pub. Date: Mar. 16, 2017

(65) Prior Publication Data
US 2018/0258388 A1 Sep. 13, 2018

(30) Foreign Application Priority Data
Sep. 8, 2015 (JP) .............................. JP2015-176896

(51) Int. Cl.
*A61K 35/30* (2015.01)
*C12N 5/079* (2010.01)
(Continued)

(52) U.S. Cl.
CPC ............ *C12N 5/0621* (2013.01); *A61K 35/30* (2013.01); *A61K 35/545* (2013.01); *A61L 27/00* (2013.01);
(Continued)

(58) Field of Classification Search
CPC .............. C12N 5/0621; C12N 2506/03; C12N 2500/90; C12N 2501/115; C12N 2501/999; A61K 35/30; A61K 35/545
See application file for complete search history.

(56) References Cited

U.S. PATENT DOCUMENTS 7,541,186 B2   6/2009   Reh et al.
7,736,896 B2   6/2010   Klimanskaya et al.
(Continued)

FOREIGN PATENT DOCUMENTS

EP   1783205 A1   5/2007
EP   2128244 A1   12/2009
(Continued)

OTHER PUBLICATIONS

Alexander et al., Eye, 29:992-1002 (2015) (Year: 2015).*
(Continued)

*Primary Examiner* — David W Berke-Schlessel
*Assistant Examiner* — Trent R Clarke
(74) *Attorney, Agent, or Firm* — Leydig, Voit & Mayer, Ltd.

(57) ABSTRACT

The present invention provides a method for more efficiently producing retinal pigment epithelial cells from pluripotent stem cells. The method of the present invention for producing retinal pigment epithelial cells includes the following steps:
(1) a first step for culturing a pluripotent stem cell in a medium comprising an FGF receptor inhibitor and/or an MEK inhibitor for a period of not more than 30 days, and (2) a second step for culturing the cell obtained in the first step in the presence of a Nodal signal transduction pathway inhibitor and/or a Wnt signal transduction pathway inhibitor to form a retinal pigment epithelial cell.

24 Claims, 14 Drawing Sheets

Specification includes a Sequence Listing.

(51) Int. Cl.
  C12Q 1/02 (2006.01)
  A61L 27/00 (2006.01)
  A61K 35/545 (2015.01)
  G01N 33/50 (2006.01)
(52) U.S. Cl.
  CPC ........... *C12Q 1/02* (2013.01); *G01N 33/5014* (2013.01); *G01N 33/5044* (2013.01); *C12N 2500/90* (2013.01); *C12N 2501/115* (2013.01); *C12N 2501/999* (2013.01); *C12N 2506/03* (2013.01)

(56) References Cited

U.S. PATENT DOCUMENTS

| | | | |
|---|---|---|---|
| 10,307,444 B2 | 6/2019 | Lanza et al. | |
| 2010/0317100 A1* | 12/2010 | Paul | C07D 403/04 435/353 |
| 2012/0003736 A1* | 1/2012 | Stern | C12N 5/0623 435/366 |
| 2013/0224156 A1 | 8/2013 | Takahashi et al. | |
| 2014/0220681 A1* | 8/2014 | Valamehr | C12N 5/0696 435/366 |
| 2014/0294778 A1 | 10/2014 | Lanza et al. | |
| 2015/0159134 A1* | 6/2015 | Choudhary | C12N 5/0621 424/93.7 |
| 2015/0175964 A1 | 6/2015 | Clegg et al. | |
| 2016/0030490 A1 | 2/2016 | Lanza et al. | |
| 2016/0175361 A1 | 6/2016 | Lanza et al. | |
| 2016/0175362 A1 | 6/2016 | Lanza et al. | |
| 2016/0237403 A1 | 8/2016 | Sawada et al. | |
| 2016/0244721 A1 | 8/2016 | Sawada et al. | |
| 2016/0264936 A1* | 9/2016 | Nakano | A61L 27/3813 |
| 2017/0313976 A1 | 11/2017 | Kuwahara et al. | |
| 2017/0313981 A1 | 11/2017 | Kuwahara et al. | |
| 2019/0060370 A1 | 2/2019 | Lanza et al. | |
| 2019/0290701 A1 | 9/2019 | Lanza et al. | |
| 2019/0321414 A1 | 10/2019 | Lanza et al. | |
| 2020/0010801 A1 | 1/2020 | Kuroda | |

FOREIGN PATENT DOCUMENTS

| | | |
|---|---|---|
| WO | WO 2004/090110 A2 | 10/2004 |
| WO | WO 2005/123902 A1 | 12/2005 |
| WO | WO 2008/048647 A1 | 4/2008 |
| WO | WO 2008/087917 A1 | 7/2008 |
| WO | WO 2012/173207 A1 | 12/2012 |
| WO | WO 2013/163171 A1 | 10/2013 |
| WO | WO 2014/121077 A2 | 8/2014 |
| WO | WO 2014/145108 A1 | 9/2014 |
| WO | WO 2015/053375 A1 | 4/2015 |
| WO | WO 2015/053376 A1 | 4/2015 |
| WO | WO 2015/054526 A2 | 4/2015 |
| WO | WO 2015/068505 A1 | 5/2015 |

OTHER PUBLICATIONS

Leach et al., Stem Cells,33:2363-2373 (2015) (Year: 2015).*
Mitsuda et al., Dev. Biol., 280:122-132 (2005) (Year: 2005).*
Nakagawa et al., Sci. Reports, 4(3594):1-7 (2014) (Year: 2014).*
Uygun et al., Crit. Rev. Biomed. Eng., 37(0): 355-375 (2009) (Year: 2009).*
Stanton et al., Mol. BioSyst., 6:44-54 (2010) (Year: 2010).*
Leach et al., Invest. Ophthalmol. Vis. Sci., 56:1002-1013 (2015) (Year: 2015).*
Buchholz et al., "Rapid and Efficient Directed Differentiation of Human Pluripotent Stem Cells into Retinal Pigmented Epithelium," *Stem Cells Transl. Med.*, 2(5): 384-393 (2013).
Chung et al., "Human Embryonic Stem Cell Lines Generated without Embryo Destruction," *Cell Stem Cell*, 2(2): 113-117 (2008).
Cohen et al., "The role of FGF-signaling in early neural specification of human embryonic stem cells," *Dev. Biol.*, 340(2): 450-458 (2010).
Eiraku et al., "Self-organizing optic-cup morphogenesis in three-dimensional culture," *Nature*, 472(7341): 51-56 (2011).
Fusaki et al., "Efficient induction of transgene-free human pluripotent stem cells using a vector based on Sendai virus, an RNA virus that does not integrate into the host genome," *Proc. Jpn. Acad., Ser. B, Phys. Biol. Sci.*, 85(8): 348-362 (2009).
Geling et al., "A γ-secretase inhibitor blocks Notch signaling in vivo and causes a severe neurogenic phenotype in zebrafish," *EMBO Rep.*, 3(7): 688-694 (2002).
Greber et al., "FGF signaling inhibits neural induction in human embryonic stem cells," *EMBO J.*, 30(24): 4874-4884 (2011).
Hirano et al., "Generation of Structures Formed by Lens and Retinal Cells Differentiating From Embryonic Stem Cells," *Dev. Dyn.*, 228(4): 664-671 (2003).
Idelson et al., "Directed Differentiation of Human Embryonic Stem Cells into Functional Retinal Pigment Epithelium Cells," *Cell Stem Cell*, 5(4): 396-408 (2009).
Ikeda et al., "Generation of $Rx^+$ / $Pax6^+$ neural retinal precursors from embryonic stem cells," *Proc. Natl. Acad. Sci. USA*, 102(32): 11331-11336 (2005).
Jadhav et al., "Notch 1 inhibits photoreceptor production in the developing mammalian retina," *Development*, 133(5): 913-923 (2006).
Kamao, "Characterization of Human Induced Pluripotent Stem Cell-Derived Retinal Pigment Epithelium Cell Sheets Aiming for Clinical Application," *Stem Cell Reports*, 2(2): 205-218 (2014).
Kawasaki et al., "Generation of dopaminergic neurons and pigmented epithelia from primate ES cells by stromal cell-derived inducing activity," *Proc. Natl. Acad. Sci. USA*, 99(3): 1580-1585 (2002).
Klimanskaya et al., "Derivation and Comparative Assessment of Retinal Pigment Epithelium from Human Embryonic Stem Cells Using Transcriptomics," *Cloning Stem Cells*, 6(3): 217-245 (2004).
Kurosawa, "Methods for Inducing Embryoid Body Formation: In Vitro Differentiation System of Embryonic Stem Cells," *J. Biosci. Bioeng.*, 103(5): 389-398 (2007).
Lamba et al., "Efficient generation of retinal progenitor cells from human embryonic stem cells," *Proc. Natl. Acad. Sci. USA*, 103(34): 12769-12774 (2006).
Livesey et al., "Vertebrate Neural Cell-Fate Determination: Lessons from the Retina," *Nat. Rev. Neurosci.*, 2(2): 109-118 (2001).
Maminishkis et al., "Confluent Monolayers of Cultured Human Fetal Retinal Pigment Epithelium Exhibit Morphology and Physiology of Native Tissue," *Invest. Ophthalmol. Vis. Sci.*, 47(8): 3612-3624 (2006).
Nakano et al., "Self-Formation of Optic Cups and Storable Stratified Neural Retina from Human ESCs," *Cell Stem Cell*, 10(6): 771-785 (2012).
Nelson et al., "Notch Activity is Downregulated Just prior to Retinal Ganglion Cell Differentiation," *Dev. Neurosci.*, 28(1-2): 128-141 (2006).
Nelson et al., "Transient inactivation of Notch signaling synchronizes differentiation of neural progenitor cells," *Dev. Biol.*, 304(2): 479-498 (2007).
Okita et al., "A more efficient method to generate integration-free human iPS cells," *Nat. Methods*, 8(5): 409-412 and supplemental "Online Methods" (2011).
Ooto et al., "Induction of the Differentiation of Lentoids from Primate Embryonic Stem Cells," *Inv. Ophthalmol. Vis. Sci.*, 44(6): 2689-2693 (2003).
Osakada et al., "Toward the generation of rod and cone photoreceptors from mouse, monkey and human embryonic stem cells," *Nat. Biotechnol.*, 26(2): 215-224 (2008).
Osakada et al., "In vitro differentiation of retinal cells from human pluripotent stem cells by small-molecule induction," *J. Cell Sci.*, 122(17): 3169-3179 (2009).
Sterneckert et al., "Neural Induction Intermediates Exhibit Distinct Roles of Fgf Signaling," *Stem Cells*, 28(10): 1772-1781 (2010).
Takahashi, "Induction of Differentiation of Human ES Cell into Retinal Cells and Regenerative Treatment: Preparation of transplantable retinal cells from human ES cells," *Igaku-no Ayumi*, 220(2): 143-146 (2007).

(56) References Cited

OTHER PUBLICATIONS

Ueno et al., "Neural conversion of ES cells by an inductive activity on human amniotic membrane matrix," *Proc. Natl. Acad. Sci. USA*, 103(25): 9554-9559 (2006).
Watanabe et al., "Directed differentiation of telencephalic precursors from embryonic stem cells," *Nat. Neurosci.*, 8(3): 288-296 (2005).
Weihofen et al., "Targeting Presenilin-type Aspartic Protease Signal Peptide Peptidase with γ-Secretase Inhibitors," *J. Biol. Chem.*, 278(19): 16528-16533 (2003).
Yaron et al., "Notch1 functions to suppress cone-photoreceptor fate specification in the developing mouse retina," *Development*, 133(7): 1367-1378 (2006).
Young et al., "A Role for Ligand-Gated Ion Channels in Rod Photoreceptor Development," *Neuron*, 41(6): 867-879 (2004).
Japanese Patent Office, International Search Report in International Patent Application No. PCT/JP2016/076524 (dated Oct. 11, 2016).
Croze et al., "Differentiation of Pluripotent Stem Cells into Retinal Pigmented Epithelium," *Dev. Ophthalmol.*, 53: 81-96 (2014).
Meyer et al., "Modeling early retinal development with human embryonic and induced pluripotent stem cells," *Proc. Natl. Acad. Sci. U.S.A.*, 106(39): 16698-16703 (2009).
European Patent Office, Extended European Search Report in European Patent Application No. 16844466.9 (dated Feb. 27, 2019).
Hu et al., "Neural differentiation of human induced pluripotent stem cells follows developmental principles but with variable potency," *Proc. Natl. Acad. Sci. U.S.A.*, 107(9): 4335-4340 (2010).
Osakada et al., "Stepwise differentiation of pluripotent stem cells into retinal cells," *Nat. Protocol.*, 4(6): 811-824 (2009).
Japanese Patent Office, International Search Report in International Patent Application No. PCT/JP2018/009093 (dated Jun. 5, 2018).
Pattamatta et al., "A mouse retinal explant model for use in studying neuroprotection in glaucoma," *Exp. Eye Res.*, 151: 38-44 (2016).
Cho et al., "Generation of retinal pigment epithelial cells from human embryonic stem cell-derived spherical neural masses," *Stem Cell Res.*, 9(2): 101-109 (2012).
Aziz et al., "Revisiting caspases in sepsis," *Cell Death Dis.*, 5(11): e1526 (2014).
Harb et al., "The Rho-Rock-Myosin Signaling Axis Determines Cell-Cell Integrity of Self-Renewing Pluripotent Stem Cells," PLoS ONE, 3(8): e3001 (2008).
Kuroda et al., "Robust induction of retinal pigment epithelium cells from human induced pluripotent stem cells by inhibiting FGF/MAPK signaling," *Stem Cell Research*, 39: 101514 (2019).
U.S. Appl. No. 16/491,746, filed Sep. 6, 2019.

* cited by examiner

| medium \ cell line | 201B7 | 1231A3 |
|---|---|---|
| AK03 | untreated  | untreated  |
| Essential 8 | untreated  | untreated  |
| StemSure hPSC Medium Δ w/o bFGF | | untreated  |

QHJI01

MEKi(PD0325901)

| 1 day | 2 days | 3 days | 4 days | 5 days | 6 days |

FGFRi(PD173074)

| 1 day | 2 days | 3 days | 4 days | 5 days | 6 days |

1231A3

MEKi(PD0325901)

| untreated | 1 day | 3 days | 6 days | 13 days |

Fig. 12

| | proportion of RPE cell in whole well (represented by 6 grades) | 0 | | 2 | | 3 | | 4 | | 1 | | 5 | |
|---|---|---|---|---|---|---|---|---|---|---|---|---|---|
| PAX6 | 235735_at | 1.0 | A | 342.5 | P | 2462.6 | P | 8152.0 | P | 93.7 | P | 2102.1 | P | 1340.7 | P | 7586.1 | P |
| PAX6 | 205646_s_at | 12.5 | A | 434.0 | P | 2109.9 | P | 9310.4 | P | 164.6 | A | 2218.6 | P | 1392.7 | P | 6747.1 | P |
| LHX2 | 206140_at | 10.1 | A | 230.3 | P | 1161.5 | P | 15479.9 | P | 59.8 | A | 2103.7 | P | 136.7 | P | 2554.7 | A |
| LHX2 | 211239_s_at | 57.8 | A | 69.6 | A | 209.9 | P | 2941.8 | P | 10.2 | A | 375.5 | P | 81.5 | A | 424.1 | A |
| SIX3 | 206634_at | 19.7 | A | 181.0 | P | 1305.6 | P | 2375.9 | P | 583.1 | P | 275.0 | P | 1072.3 | P | 467.4 | P |
| SIX3 | 242054_s_at | 4.4 | A | 581.6 | P | 6001.2 | P | 7057.9 | P | 1812.0 | P | 663.5 | P | 3601.5 | P | 1322.6 | P |

QHJI01 first step: MEKi second step

| NODALi + WNTi | NODALi | WNTi |
|---|---|---|
|  |  |  |

METHOD FOR PRODUCING RETINAL PIGMENT EPITHELIAL CELLS

CROSS-REFERENCE TO RELATED APPLICATIONS

This patent application is the U.S. national phase of International Patent Application No. PCT/JP2016/076524, filed Sep. 8, 2016, which claims the benefit of Japanese Patent Application No. 2015-176896, filed on Sep. 8, 2015, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,975 bytes ASCII (Text) file named "738490SequenceListing.txt," created Feb. 28, 2018.

TECHNICAL FIELD

The present invention relates to a method of producing a retinal pigment epithelial (RPE) cell and the like.

BACKGROUND ART

Retinal pigment epithelial cells are pigment epithelial cells that are present in the outermost layer of retina, and play an important role in the maintenance of photoreceptor cells such as phagocytosis of outer segment of photoreceptor cells and recycle of visual substances, and the like. Age-related macular degeneration caused by abnormality of retinal pigment epithelial cells due to aging and the like is an ophthalmic disease that causes central visual loss or blindness, and it has been desired to develop an effective method for treating same. Recently, cell transplantation therapy supplementing or substituting retinal pigment epithelial cells has attracted a lot of attention as a novel method for treating age-related macular degeneration, and it has been expected to utilize retinal pigment epithelial cells as a grafting material for cell therapy. To date, while some reports on a method of inducing differentiation into retinal pigment epithelial cells using human pluripotent stem cells have been made (nonpatent documents 1 and 2, patent documents 1, 2, 3 and 4), a more efficient and convenient production method has been desired, since a technology for stably producing high-quality retinal pigment epithelial cells in large amounts is required in regenerative medicine industry.

DOCUMENT LIST

Patent Documents patent document 1: WO 2012/173207
patent document 2: WO 2015/053375
patent document 3: WO 2015/053376
patent document 4: US 2013/0224156

Non-Patent Document non-patent document 1: Stem Cell Reports, 2(2), 205-218 (2014)
non-patent document 2: Cell Stem Cell, 10(6), 771-785 (2012)

SUMMARY OF THE INVENTION

Problems to be Solved by the Invention

In order to stably produce a large amount of retinal pigment epithelial cells derived from pluripotent stem cells, when said cells are used for regenerative medicine and the like, it is urgently needed to develop a more efficient method.

Means of Solving the Problems

In view of the circumstances, the present inventors conducted intensive studies, which resulted in the completion of the present invention.

That is, the present invention relates to the following.

[1] A production method of a retinal pigment epithelial cell comprising the following steps:
(1) a first step for culturing a pluripotent stem cell in a medium comprising an FGF receptor inhibitor and/or an MEK inhibitor for a period of not more than 30 days, and
(2) a second step for culturing the cell obtained in the first step in the presence of a Nodal signal transduction pathway inhibitor and/or a Wnt signal transduction pathway inhibitor to form a retinal pigment epithelial cell.

[2] The production method according to the above-mentioned [1], wherein the first step is performed in serum-free conditions.

[3] The production method according to the above-mentioned [1] or [2], wherein the first step is performed in the absence of feeder cells.

[4] The production method according to any of the above-mentioned [1] to [3], wherein the medium in the first step further comprises a factor for maintaining undifferentiated state.

[5] The production method according to the above-mentioned [4], wherein the factor for maintaining undifferentiated state is an FGF signal transduction pathway agonist.

[6] The production method according to the above-mentioned [5], wherein the FGF signal transduction pathway agonist is bFGF.

[7] The production method according to any of the above-mentioned [1] to [6], wherein the FGF receptor inhibitor is at least one kind selected from the group consisting of PD173074 and SU5402.

[8] The production method according to any of the above-mentioned [1] to [7], wherein the MEK inhibitor is at least one kind selected from the group consisting of PD0325901, PD184352, U0126, TAK-733 and AZD-8330.

[9] The production method according to any of the above-mentioned [1] to [8], wherein the Nodal signal transduction pathway inhibitor is an Alk4, 5 or 7 inhibitor.

[10] The production method according to the above-mentioned [9], wherein the ALK4, 5 or 7 inhibitor is SB431542.

[11] The production method according to any of the above-mentioned [1] to [10], wherein the Wnt signal transduction pathway inhibitor is CKI-7.

[12] The production method according to any of the above-mentioned [1] to [11], wherein the pluripotent stem cell is a primate pluripotent stem cell.

[13] The production method according to any of the above-mentioned [1] to [12], wherein the pluripotent stem cell is a human pluripotent stem cell.

[14] The production method according to any of the above-mentioned [1] to [13], wherein the medium in the first step further comprises a BMP receptor inhibitor.
[15] The production method according to the above-mentioned [14], wherein the BMP receptor inhibitor is an ALK2/3 inhibitor.
[16] The production method according to the above-mentioned [15], wherein the ALK2/3 inhibitor is LDN193189.
[17] The production method according to any of the above-mentioned [1] to [16], wherein the medium in the first step further comprises a Sonic hedgehog signal transduction pathway agonist.
[18] The production method according to the above-mentioned [17], wherein the Sonic hedgehog signal transduction pathway agonist is SAG.
[19] The production method according to any of the above-mentioned [1] to [18], wherein the medium in the first step further comprises a PKC inhibitor.
[20] The production method according to the above-mentioned [19], wherein the PKC inhibitor is Go6983.
[21'] The production method according to any of the above-mentioned [1] to [20], wherein the culture period in the first step is a period sufficient for inducing gene expression of at least one of eye field transcription factors and of not more than 30 days.
[22'] The production method according to any of the above-mentioned [1] to [20], wherein the culture period in the first step is a period sufficient for inducing gene expression of at least one of PAX6, LHX2 and SIX3 and of not more than 30 days.
[21] The production method according to any of the above-mentioned [1] to [20], [21'] and [22'], wherein the culture period in the first step is for 2 days-13 days.
[22] The production method according to any of the above-mentioned [1] to [21], [21'] and [22'], wherein the culture period in the first step is for 4 days-6 days.
[23] A reagent for evaluating toxicity or efficacy of a test substance comprising a retinal pigment epithelial cell produced by the production method according to any of the above-mentioned [1] to [22], [21'] and [22'].
[24C] A method of evaluating toxicity or efficacy of a test substance comprising contacting a retinal pigment epithelial cell produced by the production method according to any of the above-mentioned [1] to [22], [21'] and [22'] with the substance, and assaying the effect of the substance on the cells.
[25] An agent for treating a disease based on disorder of retinal pigment epithelial cells, comprising a retinal pigment epithelial cell produced by the production method according to any of the above-mentioned [1] to [22], [21'] and [22'].
[26] A method of treating a disease based on disorder of retinal pigment epithelial cells, comprising transplanting into a subject in need thereof an effective amount of retinal pigment epithelial cells produced by the production method according to any of the above-mentioned [1] to [22], [21'] and [22'].
[27] A retinal pigment epithelial cell produced by the production method according to any of the above-mentioned [1] to [22], [21'] and [22'] for use in the treatment of a disease based on disorder of retinal pigment epithelial cells.
[28] A pharmaceutical composition comprising a retinal pigment epithelial cell produced by the production method according to any of the above-mentioned [1] to [22], [21'] and [22'] as an active ingredient.

Effect of the Invention

The present invention has made it possible to provide a more efficient method of producing retinal pigment epithelial cells than existing differentiation induction methods. Therefore, the method of the present invention is useful in terms of efficient production of retinal pigment epithelial cells that can be a grafting material for cell therapy, or a reagent or material used for evaluating toxicity or efficacy of a chemical substance and the like.

BRIEF DESCRIPTION OF THE DRAWINGS

FIG. 12 shows percentages of iPS cell (Ff-I01 or QHJI01)-derived retinal pigment epithelial (RPE) cells, which were produced by a production method comprising an MEK inhibitor or FGF receptor inhibitor treatment step using "StemFit®" AK03N medium, in a whole well after 43 days of culture, which percentages are results by visual judgment according to FIG. 8A, and expression values (Signal) and flags (Detection) of PAX6, LHX2 and SIX3 upon termination of the first step (MEKi or FGFRi). For comparison, results of visual judgment of percentages of RPE cells in a whole well of iPS cell-derived differentiated cells produced by a production method without an MEK inhibitor and/or FGF receptor inhibitor treatment step, and expression values (Signal) and flags (Detection) of PAX6, LHX2 and SIX3 upon a time corresponding to termination of the first step are shown (untreated). MEKi: MEK inhibitor (1 μM PD0325901), FGFRi: FGF receptor inhibitor (100 nM PD173074).

DESCRIPTION OF EMBODIMENTS

1. Definition

Figure 1:
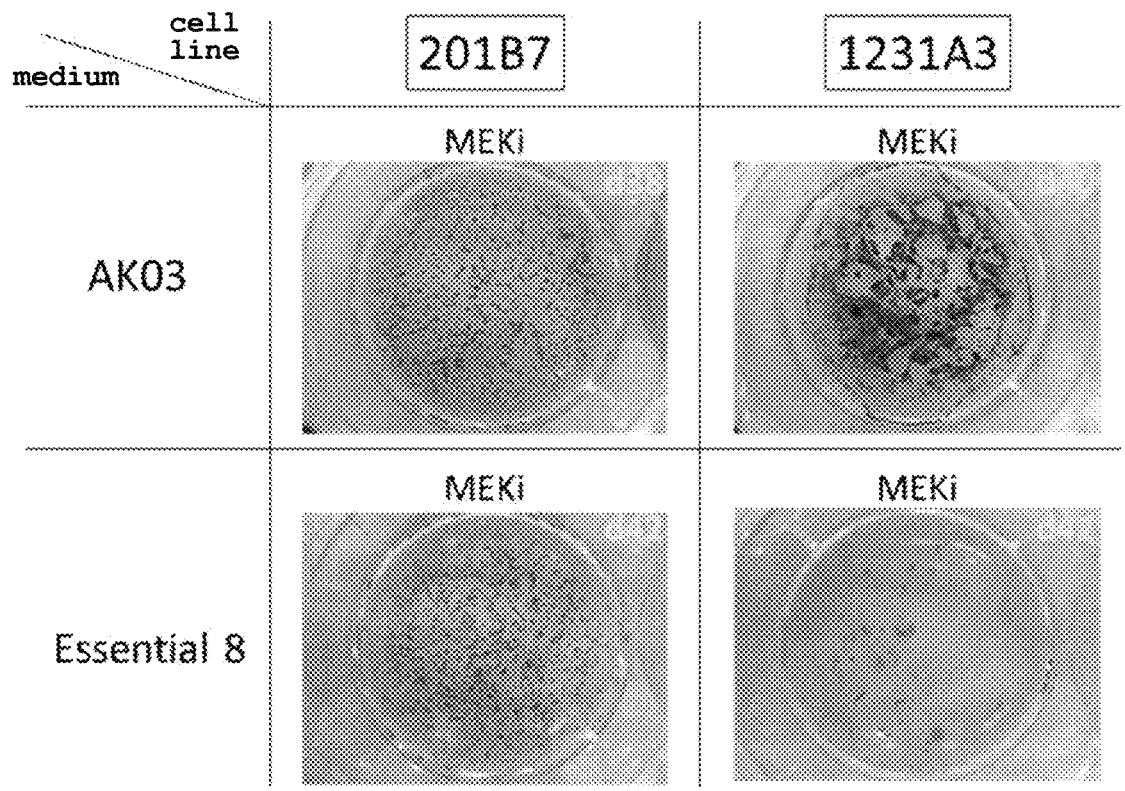
FIG. 1 shows photographs of 6-well culture plates after 38-42 days of culture containing iPS cell (201B7 or 1231A3)-derived retinal pigment epithelial (RPE) cells produced by a production method comprising an MEK inhibitor treatment step using "StemFit®" AK03 medium or Essential 8 medium. MEKi: MEK inhibitor (1 µM PD0325901 when "SternFit®" AK03 medium was used; 0.03 µM PD0325901 when Essential 8 medium was used)

In the present invention, "pluripotent stem cell" means a cell having self-renewal ability and pluripotency, a stem cell capable of being cultured in vitro and having an ability to differentiate into all of cell lineages belonging to three germ layers (ectoderm, mesoderm, endoderm) (pluripotency).

Examples of the pluripotent stem cell include embryonic stem cell (ES cell), induced pluripotent stem cell (iPS cell) and the like. The pluripotent stem cells to be used in the present invention are mammalian pluripotent stem cells, preferably pluripotent stem cells of rodents or primates, more preferably human pluripotent stem cells. As the mammal here, primates such as human, monkey and the like, rodents such as mouse, rat, hamster, guinea pig and the like, and other canine, cat, swine, bovine, goat, horse, sheep, rabbit and the like can be mentioned.

Embryonic stem cells can be produced by, for example, culturing an inner cell mass present in the blastocyst stage embryo before implantation on a feeder cell or in a medium containing LIF. Specific production methods of embryonic stem cells are described in, for example, WO 96/22362, WO 02/101057, U.S. Pat. Nos. 5,843,780, 6,200,806, 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an enucleated egg.

The "induced pluripotent stem cell" is a cell induced to have pluripotency by reprogramming a somatic cell by a known method and the like. Specifically, a cell induced to have pluripotency by reprogramming somatic cells such as fibroblast, skin cell, peripheral blood mononuclear cell and the like by the introduction of any combinations of a plurality of reprogramming factors selected from genes such as Oct3/4, Sox2, Klf4, Myc (c-Myc, N-Myc, L-Myc), Glis1, Nanog, Sa114, lin28, Esrrb and the like can be mentioned. Examples of preferable combination of reprogramming factors can include (1) Oct3/4, Sox2, Klf4, and Myc (c-Myc or L-Myc), and (2) Oct3/4, Sox2, Klf4, Lin28 and L-Myc (Stem Cells, 2013; 31:458-466).

Induced pluripotent stem cell was first established by Yamanaka et al. in mouse cell in 2006 (Cell, 2006, 126(4), pp. 663-676) and also established in human fibroblast in 2007 (Cell, 2007, 131(5) pp. 861-872; Science, 2007, 318 (5858) pp. 1917-1920; Nat. Biotechnol., 2008, 26(1) pp. 101-106). Various improvements have thereafter been made in the induction method of induced pluripotent stem cells and a specific production method of, for example, a mouse induced pluripotent stem cell is described in Cell. 2006 Aug. 25; 126(4):663-76, and that of a human induced pluripotent stem cell is described in Cell. 2007 Nov. 30; 131(5):861-72 and the like.

Besides the production method based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 201B7-Ff cell, 253G1 cell, 253G4 cell, 1201C1 cell, 1205D1 cell, 1210B2 cell or, 1231A3 cell and the like are available from Kyoto University and iPS Academia Japan, Inc. As the established induced pluripotent stem cell, for example, Ff-I01 cell and Ff-I14 cell and QHJI01 cell established by Kyoto University are available from Kyoto University.

While the somatic cell used for obtaining induced pluripotent stem cell is not particularly limited, fibroblast, blood-lineage cell (e.g., peripheral blood mononuclear cell or T cell, cord blood-derived cell) and the like can be specifically mentioned. As the fibroblast, those derived from dermis and the like can be mentioned.

When induced pluripotent stem cell is produced by reprogramming by the expression of several kinds of reprogramming factors, the means for gene expression is not particularly limited. A gene transfer method or a direct injection method of protein, which are well known to those of ordinary skill in the art, can be used. Specific examples of the aforementioned gene transfer method include an infection method using a virus vector (e.g., retrovirus vector, lentivirus vector, Sendaivirus vector, adenovirus vector, adeno-associated virus vector), a calcium phosphate method, lipofection method, RetroNectin method, electroporation method, each using a plasmid vector (e.g., plasmid vector, episomal vector) or RNA vector, and the like.

An induced pluripotent stem cell can be produced in the presence of a feeder cell or in the absence of feeder cells (feeder-free). When an induced pluripotent stem cell is produced in the presence of a feeder cell, the induced pluripotent stem cell can be produced by a known method in the presence of a factor for maintaining undifferentiated state. While a medium to be used for producing an induced pluripotent stem cell in the absence of feeder cells is not particularly limited, a known maintenance medium for embryonic stem cells and/or induced pluripotent stem cells, and a medium for establishing induced pluripotent stem cell under feeder-free can be used. Examples of the medium for establishing an induced pluripotent stem cell under feeder-free conditions can include feeder-free media such as Essential 8 medium (E8 medium), Essential 6 medium, TeSR medium, mTeSR medium, mTeSR-E8 medium, Stabilized Essential 8 medium, StemFit® and the like. When an induced pluripotent stem cell is produced, for example, it can be produced by gene transfer of 4 factors of Oct3/4, Sox2, Klf4, and Myc into somatic cell by using a Sendai-virus vector in the absence of feeder cells.

The pluripotent stem cell to be used in the present invention is preferably induced pluripotent stem cell of rodents or primates, more preferably human induced pluripotent stem cell.

While those of ordinary skill in the art can perform maintenance culture or expansion culture of pluripotent stem cells by a well-known method, pluripotent stem cells are preferably subjected to maintenance culture or expansion culture under serum-free conditions and in the absence of feeder cells from the aspects of the safety of graft cell production and the like.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of pigment epithelial cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODO-SHA CO., LTD. (1995); and so on.

To be specific, for example, the genomic DNA comprising the target gene to be modified (e.g., cell marker gene, histocompatibility antigen gene, disease-related gene and so on) is isolated, and a targeting vector used for homologous recombination of the target gene is produced using the isolated genomic DNA. The produced targeting vector is introduced into stem cells and the cells that showed homologous recombination between the target gene and the targeting vector are selected, whereby stem cells having the modified gene on the chromosome can be produced.

Examples of the method for isolating genomic DNA comprising the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic DNA comprising the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targeting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targeting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

The "eye field transcription factor" in the present invention is a gene expressed in the eye field region in an early developmental stage, and ET(Tbx3), Rx1(Rax), Pax6, Six3, Lhx2, Tlx(Nr2e1), Optx2(Six6) and the like have been identified. These eye field transcription factors can be used as markers of early eye formation stage.

The "retinal pigment epithelial cell" in the present invention means an epithelial cell present on the outside of neural retinal tissues in retina in vivo. Whether the cell is a retinal pigment epithelial cell can be easily confirmed by those of ordinary skill in the art based on, for example, the expression of cell markers (RPE65, Mitf, CRALBP, MERTK, BEST1 etc.), presence of melanin granules (brown-black), intercellular tight junction, characteristic polygonal, cobblestone-like cell morphology and the like. Whether the cell has a function of retinal pigment epithelial cell can be easily confirmed by the secretory capacity of cytokines such as VEGF and PEDF and the like, and the like.

The "suspension culturing" in the present invention refers to culturing under conditions for maintaining a state in which cells or cell aggregates are suspended in a culture medium. That is, culturing is performed under conditions in which a strong cell-substratum junction is not formed between a cell or cell aggregate and a culture vessel and the like.

The "adhesion culturing" refers to culturing under conditions in which a cell or cell aggregate is adhered to a culture vessel material and the like. In this case, adhesion of cell means that a strong cell-substratum junction is formed between a cell or cell aggregate and a culture vessel material. That is, adhesion culturing refers to culturing under conditions in which a strong cell-substratum junction is formed between a cell or cell aggregate and a culture vessel material and the like.

In a cell aggregate in suspension culture, a planar cell-cell adhesion is formed. In cell aggregates in suspension culture, a cell-substratum junction is hardly formed with a culture vessel and the like and, even if it is formed, its contribution is small. In some embodiment, in a cell aggregate in suspension culture an endogenous cell-substratum junction is present inside the aggregate, but a cell-substratum junction is hardly formed with a culture vessel and the like and, even if it is formed, its contribution is small. The planar cell-cell adhesion (plane attachment) means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion molecules (e.g., E-cadherin and N-cadherin).

A culture vessel used for adhesion culturing is not particularly limited as long as "adhesion culturing" can be performed, and those of ordinary skill in the art can appropriately select a culture vessel suitable according to the culture scale, culture conditions and period for the culturing. Examples of such culture vessel include tissue culture flasks, culture dishes, tissue culture dishes, multi-dishes, microplates, micro-well plates, multi-plates, multi-well plates, chamber slides, schale, tubes, trays, culture bags, microcarriers, beads, spinner flasks and roller bottles. To enable adhesion culturing, these culture vessels are preferably cell-adhesive. Cell-adhesive culture vessels include culture vessels whose surfaces have been artificially treated to improve cell adhesiveness, and specifically, a culture vessel whose inside is coated with a coating agent can be mentioned. Examples of the coating agent include extracellular matrix such as laminin [including laminin α5β1γ1 (hereinafter laminin 511), laminin α1β1γ1 (hereinafter laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like, and the like. It is also possible to use a culture container whose surface is processed by a positive electric charge treatment and the like. More preferably, a culture vessel coated with laminin 511E8 is used since stable and efficient induction of retinal pigment epithelial cells can be performed (WO 2015/053375). As laminin 511E8, a commercially available product (e.g., iMatrix-511, Nippi) can be used.

The culture vessel to be used when performing suspension culturing is not particularly limited as long as it enables "culturing in suspension" and those of ordinary skill in the art can appropriately determine same. Examples of such culture vessel include flask, tissue culture flask, dish, petri dish, tissue culture dish, multidish, microplate, microwell plate, micropore, multiplate, multiwell plate, chamber slide, schale, tube, tray, culture bag, spinner flask, roller bottle and so on. To enable suspension culturing, these culture vessels are preferably non-cell-adhesive. Non-cell-adhesive culture vessels include culture vessels whose surfaces have not undergone an artificial treatment for improving the cell adhesiveness (e.g., coating treatment with extracellular matrix such as laminin, entactin, collagen, gelatin etc., and the like, or with polymer such as polylysine, polyornithine etc. and the like or surface processing such as positive electric charge treatment and the like), and the like. As a non-cell-adhesive culture vessel, culture vessels whose surfaces have been artificially treated to decrease adhesiveness to the cells (e.g., superhydrophilic treatment with MPC polymer and the like, protein low adsorption treatment etc.) and the like can be used.

The medium to be used for culturing cells in the present invention can be prepared from a medium generally used for culturing animal cells as a basal medium. Examples of the commercially available basal medium include media that can be used for culturing animal cells such as BME medium, BGJb medium, CMRL 1066 medium, Glasgow MEM (GMEM) medium, Improved MEM Zinc Option medium, IMDM medium, Medium 199 medium, Eagle MEM medium, αMEM medium, DMEM medium, F-12 medium, DMEM/F-12 medium, IMDM/F12 medium, Ham medium, RPMI 1640 medium, Fischer's medium and the like. A single medium or a combination of two or more kinds thereof can be used, but the medium is not limited thereto.

The "serum medium" in the present invention means a medium containing unadjusted or unpurified serum. While a serum derived from any animal can be used, a serum derived from mammals such as bovine, human and the like can be preferably used. When performing culture aiming at autologous transplantation is performed, the patient's own serum can also be used.

The concentration of the serum is not particularly limited as long as it can efficiently induce differentiation of retinal pigment epithelial cells. For example, it can be appropriately set in the range of about 0.5%-30% (v/v). The concentration may be constant or may be changed in steps.

The "serum-free medium" means a medium not containing an unadjusted or unpurified serum. In the present invention, a medium containing purified blood-derived components and animal tissue-derived components (e.g., growth factor) is also included in the serum-free medium unless unadjusted or unpurified serum is contained therein.

The "serum-free conditions" means conditions free of unadjusted or unpurified serum, specifically, conditions using a serum-free medium.

The serum-free medium may contain a serum replacement. Examples of the serum replacement include one appropriately containing albumin, transferrin, fatty acid, collagen precursor, trace element, 2-mercaptoethanol or 3' thiolglycerol, or equivalents of these etc., and so on. Such serum replacement may be prepared by, for example, the method described in WO 98/30679. The serum replacement may be a commercially available product. Examples of such commercially available serum replacement include Knockout™ Serum Replacement (Life Technologies, hereinafter sometimes to be indicated as KSR), Chemically Defined Lipid Concentrate (manufactured by Life Technologies) and Glutamax™ (manufactured by Life Technologies), B27 (manufactured by Life Technologies), N2 (manufactured by Life Technologies).

To avoid complicated preparation, a serum-free medium added with an appropriate amount (e.g., about 0.5% to about 30%, preferably about 5% to about 20%) of commercially available KSR (manufactured by Life Technologies) (e.g., Glasgow MEM medium added with KSR in the above-mentioned concentration range) may be used as such serum-free medium.

The medium to be used in the present invention may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

The medium to be used in the present invention optionally contains, in addition to those mentioned above, a ROCK (Rho-associated coiled-coil forming kinase/Rho-associated kinase) inhibitor to suppress cell death (apoptosis) of the pluripotent stem cells. As the ROCK inhibitor, Y-27632, Fasudil or H-1152 can be mentioned. The concentration of the ROCK inhibitor can be appropriately set by those of ordinary skill in the art. For example, it can be set within a concentration range showing a ROCK inhibitory activity corresponding to about 50 nM-200 µM of Y-27632.

To avoid contamination with a chemically-undefined component, a medium to be used in the present invention is preferably a medium whose components are chemically-defined (Chemically defined medium; CDM).

In the present invention, the culturing is preferably performed under xeno-free conditions. The "xeno-free" means conditions eliminating components (protein etc.) derived from species different from that of the cell to be cultured.

In the present invention, the "medium containing substance X" and "in the presence of substance X" refer to a medium supplemented with an exogenous substance X or a medium containing an exogenous substance X, or in the presence of an exogenous substance X. That is, when the cells present in the medium endogenously express, secrete or produce substance X, the endogenous substance X is distinguished from the exogenous substance X, and a medium free of exogenous substance X is understood to fall outside the category of the "medium containing substance X", even when it contains endogenous substance X.

For example, a "medium containing a FGF signal transduction pathway agonist" is a medium supplemented with an exogenous FGF signal transduction pathway agonist or a medium containing an exogenous FGF signal transduction pathway agonist.

In the present invention, a "feeder cell" refers to a cell other than a pluripotent stem cell that co-exists when culturing the stem cell. Examples of the feeder cells used for culturing pluripotent stem cells while maintaining undifferentiated state include mouse fibroblasts (MEF), human fibroblasts, SNL cells and the like. As the feeder cells, feeder cells that underwent a growth suppression treatment is preferable. Examples of the growth suppression treatment include treatment with a growth inhibitor (e.g., mitomycin C), gamma irradiation and the like. Feeder cells used for culturing pluripotent stem cells while maintaining undifferentiated state contributes to the maintenance of undifferentiation state of pluripotent stem cell by secretion of a humoral factor (preferably factor for maintaining undifferentiated state), or production of a scaffold for cell adhesion (extracellular substrate).

In the present invention, in the absence of feeder cells (feeder-free) means culturing in the absence of feeder cells. As the absence of a feeder cell, for example, conditions not added with a feeder cell or substantially free of a feeder cell (e.g., the ratio of number of feeder cells relative to the total number of cells is not more than 3%) can be mentioned.

2. Production Method of Retinal Pigment Epithelial Cells

The production method of the present invention is a method for producing retinal pigment epithelial cells, comprising the following steps (1)-(2):
(1) a first step for culturing pluripotent stem cells in a medium containing an FGF receptor inhibitor and/or an MEK inhibitor for a period not exceeding 30 days, and
(2) a second step for culturing the cells obtained in the first step in the presence of a Nodal signal transduction pathway inhibitor and/or a Wnt signal transduction pathway inhibitor to form retinal pigment epithelial cells.
(1) The first Step As a preferable pluripotent stem cell in the first step, induced pluripotent stem cell, more preferably human induced pluripotent stem cell can be mentioned. The production method of induced pluripotent stem cells is not particularly limited, and it can be produced by a method well known to those of ordinary skill in the art as mentioned above. It is also desirable to perform a step for preparing induced pluripotent stem cells (that is, a step of reprogramming somatic cells to establish pluripotent stem cells) under feeder-free condition.

Pluripotent stem cell is generally subjected to the first step after maintenance culturing or expansion culturing. The maintenance culturing or expansion culturing of pluripotent stem cells can be performed by a method well known to those of ordinary skill in the art, preferably in the absence of feeder cells. While the maintenance and expansion culturing of pluripotent stem cells can be performed by adhesion culturing or suspension culturing, it is preferably performed by adhesion culturing.

The maintenance culturing or expansion culturing of pluripotent stem cells in the absence of feeder cells can be performed in a medium containing a factor for maintaining undifferentiated state. The factor for maintaining undifferentiated state is not particularly limited as long as it is a substance having an action to suppress differentiation of pluripotent stem cells. It is generally a factor for maintaining undifferentiated state derived from a mammal. Since the factor for maintaining undifferentiated state may have cross-reactivity among mammal species, a factor for maintaining undifferentiated state of any mammal may also be used as long as the undifferentiated state of the pluripotent stem cells to be cultured can be maintained. Preferably, a factor for maintaining undifferentiated state of a mammal of the same species as the cells to be cultured is used.

Examples of the factor for maintaining undifferentiated state widely used by those of ordinary skill in the art include a FGF signal transduction pathway agonist, a TGFβ family signal transduction pathway agonist and the like in the case of primed pluripotent stem cells (e.g., human ES cells, human iPS cells). As the FGF signal transduction pathway agonist, fibroblast growth factors (e.g., bFGF, FGF4, FGF8) can be specifically mentioned. As the TGFβ family signal transduction pathway agonist, a TGFβ signal transduction pathway agonist (e.g., TGFβ1, TGFβ2), a Nodal/Activin signal transduction pathway agonist (e.g., Nodal, Activin A, Activin B) can be mentioned. When human pluripotent stem cells (human ES cells, human iPS cells) are cultured, the factor for maintaining undifferentiated state is preferably bFGF.

The concentration of the factor for maintaining undifferentiated state in the medium to be used in the maintenance culturing or expansion culturing of pluripotent stem cells is a concentration capable of maintaining the undifferentiated state of the pluripotent stem cells to be cultured, and can be appropriately determined by those of ordinary skill in the art. For example, specifically, when bFGF is used as a factor for maintaining undifferentiated state, the concentration thereof is generally about 4-500 ng/mL, preferably 10-200 ng/mL, more preferably about 30-150 ng/mL.

As a medium containing a factor for maintaining undifferentiated state (hereinafter sometimes to be indicated as a feeder-free medium), a medium commercially available as a medium for stem cell can also be used as appropriate. For example, Essential 8 (manufactured by Life Technologies), hESF9 (Proc Natl Acad Sci USA. 2008 Sep. 9; 105(36): 13409-14), S-medium (manufactured by DS Pharma Biomedical), StemPro (manufactured by Life Technologies), mTeSR1 (manufactured by STEMCELL Technologies), mTeSR2 (manufactured by STEMCELL Technologies), TeSR-E8 (manufactured by STEMCELL Technologies) and the like are commercially available. In addition to these, StemFit® (manufactured by Ajinomoto Co., Inc.) can be mentioned as a feeder-free medium under development. Using these media, maintenance culturing or expansion culturing of pluripotent stem cells can be performed.

When the pluripotent stem cells that underwent maintenance culturing or expansion culturing are recovered, dispersed pluripotent stem cells are prepared by a dispersion operation. A dispersion operation of the pluripotent stem cells may contain mechanical dispersion treatment, cell dispersion solution treatment, and cell protecting agent addition treatment. These treatments may be performed in combination. Preferably, a cell dispersion solution treatment is performed simultaneously with a cell protecting agent addition treatment and then a mechanical dispersion treatment is performed.

As a cell protecting agent to be used for the cell protecting agent addition treatment, heparin, serum, or serum replacement can be mentioned. Also, to suppress cell death induced by dispersion (particularly, cell death of human pluripotent stem cells), a ROCK inhibitor may be added during dispersion. As the ROCK inhibitor, Y-27632, Fasudil (HA1077), H-1152 and the like can be mentioned.

As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of mechanical dispersion treatment, a pipetting treatment or scraping by a scraper can be mentioned.

The dispersed pluripotent stem cells can be seeded in a new culture container and subjected to the first step.

To suppress cell death induced by dispersion (particularly, cell death of human pluripotent stem cells), the pluripotent stem cells may be seeded in a new culture container, maintenance culturing may be continuously performed in the presence of a ROCK inhibitor, and the first step may be started thereafter. While the period of the treatment with a ROCK inhibitor is not particularly limited as long as the cell death induced by dispersion can be suppressed, it is generally about 12-24 hr.

The concentration of the pluripotent stem cells when the first step is started can be appropriately set by those of ordinary skill in the art. In adhesion culture, it is, for example, $1.0 \times 10^2$ cells/cm$^2$ to $1 \times 10^6$ cells/cm$^2$, preferably $2.0 \times 10^2$ cells/cm$^2$ to $2 \times 10^5$ cells/cm$^2$, more preferably $5 \times 10^2$ cells/cm$^2$ to $1 \times 10^5$ cells/cm$^2$ or $1 \times 10^3$ cells/cm$^2$ to $1 \times 10^4$ cells/cm$^2$.

To avoid contamination with a chemically-undefined component, a medium to be used in the first step is preferably a medium whose components are chemically-defined.

A medium to be used in the first step may be a serum medium or a serum-free medium. To avoid contamination with a chemically-undefined component, it is preferably a serum-free medium.

The medium used in the first step optionally contains a ROCK (Rho-associated coiled-coil forming kinase/Rho-associated kinase) inhibitor to suppress cell death (apoptosis). As the ROCK inhibitor, Y-27632, Fasudil or H-1152 can be mentioned. Only one kind of a ROCK inhibitor may be used or two or more kinds thereof may be used in combination. While the concentration of the ROCK inhibitor can be appropriately set by those of ordinary skill in the art, for example, it can be set within the concentration range showing a ROCK inhibitory activity corresponding to about 50 nM-200 µM of Y-27632.

The culturing in the first step may be performed in the presence of a feeder cell. To avoid contamination of chemically-undefined components, the culturing is preferably performed under conditions free of a feeder cell.

The medium used in the first step may or may not contain a foreign factor for maintaining undifferentiated state irrespective of whether it is culturing in the absence of feeder cells or in the presence of a feeder cell. The first step in the present invention is more preferably performed in a medium containing a factor for maintaining undifferentiated state and in the absence of feeder cells. The factor for maintaining undifferentiated state is not particularly limited as long as it is a substance having an action to suppress differentiation of pluripotent stem cells. Preferably, it contains an FGF signal transduction pathway agonist, more preferably bFGF.

The concentration of the factor for maintaining undifferentiated state in the medium to be used in the first step may be in the concentration range of the factor for maintaining undifferentiated state used for maintenance culturing or expansion culturing of pluripotent stem cells. For example, when bFGF is used as a factor for maintaining undifferentiated state in the absence of feeder cells, the concentration thereof is generally about 4-500 ng/mL, preferably 10-200 ng/mL, more preferably about 30-150 ng/mL.

The medium to be used in the first step contains an FGF receptor inhibitor and/or an MEK inhibitor. The medium can contain a further component (e.g., any agonist or inhibitor of signal transduction pathway) as long as the production efficiency of retinal pigment epithelial cells by the production method of the present invention is not markedly decreased (e.g., the same level as or not more than the level of efficiency without the first step). For example, the medium may further contain a BMP receptor inhibitor, a Sonic hedgehog signal transduction pathway agonist or a PKC inhibitor singly or in the combination of any of the following (1)-(4): (1) BMP receptor inhibitor and Sonic hedgehog signal transduction pathway agonist, (2) BMP receptor inhibitor and PKC inhibitor, (3) Sonic hedgehog signal transduction pathway agonist and PKC inhibitor, (4) BMP receptor inhibitor, Sonic hedgehog signal transduction pathway agonist and PKC inhibitor.

In the present invention, FGF receptor inhibitor is not particularly limited as long as it is a substance capable of suppressing signal transduction mediated by FGF, and may be any of protein, nucleic acid and low-molecular-weight compound. FGF here forms a family containing at least 22 species. As the representative FGF receptor, FGFR1, FGFR2, FGFR3, FGFR4 and the like can be mentioned, and the FGF receptor inhibitor is a substance that inhibits one, a plurality or all of these. Examples of the substance include, but are not limited to, a substance that directly acts on FGF or FGF receptor (e.g., antibody, aptamer etc.), a substance that suppresses expression of a gene encoding FGF or FGF receptor (e.g., antisense oligonucleotide, siRNA etc.), a substance that inhibits binding of FGF receptor and FGF (e.g., soluble FGF receptor, FGF antagonist etc.), a substance that inhibits physiological activity caused by signal transduction by FGF receptor [for example, low-molecular-weight compounds such as PD173074 (N-[2-[[4-(Diethylamino)butyl]amino]-6-(3,5-dimethoxyphenyl)pyrido[2,3-d]pyrimidin-7-yl]-N'-(1,1-dimethylethyl)urea), SU5402 (2-[(1,2-Dihydro-2-oxo-3H-indol-3-ylidene)methyl]-4-methyl-1H-pyrrole-3-propanoic acid) and the like] that inhibit tyrosine kinase activity of FGF receptor by ATP competition. Only one kind of the substance may be used or two or more kinds thereof may be used in combination. PD173074 and SU5402 are known FGF receptor inhibitors, and a commercially available product and the like can be obtained as appropriate. As the FGF receptor inhibitor, preferred is, for example, PD173074 or SU5402.

In the present invention, the concentration of the FGF receptor inhibitor contained in the medium is not particularly limited as long as retinal pigment epithelial cells can be produced by the method of the present invention, and can be appropriately determined by those of ordinary skill in the art according to the kind of the FGF receptor inhibitor. For example, the concentration of the FGF receptor inhibitor is in a concentration range showing an FGF receptor inhibitory activity corresponding to 1-1000 nM, preferably 10-500 nM, more preferably 25 nM-400 nM, particularly preferably 30-300 nM, of PD173074. For example, a concentration range of 0.1-500 µM, preferably 1-100 µM, more preferably 5-20 µM, of SU5402 can be mentioned. The concentration may be constant through the first step or may be varied in steps as long as retinal pigment epithelial cells can be produced by the method of the present invention.

In the present invention, the MEK inhibitor is not particularly limited as long as it is a substance that inhibits expression or activity of MEK family, and may be any of protein, nucleic acid and low-molecular-weight compound. As the representative MEK family, MEK1, MEK2, MEK3 and the like can be mentioned, and the MEK inhibitor is a substance that inhibits the expression or activity of one, a plurality or all of these MEK families. Examples of the substance include, but are not limited to, a substance that suppresses expression of a gene encoding various MEK (e.g., antisense oligonucleotide, siRNA etc.), a substance that inhibits enzyme activity of various MEK [low-molecular-weight compounds such as PD0325901 (N-[(2R)-2,3-Dihydroxypropoxy]-3,4-difluoro-2-[(2-fluoro-4-iodophenyl)amino]-benzamide), PD184352 ((2-[(2-Chloro-4-iodophenyl)amino]-N-cyclopropylmethoxy)-3,4-difluorobenzamide), PD98059 (2'-Amino-3'-Methoxyflavone), U0126 (1,4-Diamino-2,3-dicyano-1,4-bis[2-aminophenylthio]butadiene), MEK162 (5-[(4-Bromo-2-fluorophenyl)amino]-4-fluoro-N-(2-hydroxyethoxy)-1-methyl-1H-benzimidazole-6-carboxamide), SL327 (α-[Amino[(4-aminophenyl)thio]methylene]-2-(trifluoromethyl)benzeneacetonitrile), TAK-733 ((R)-3-(2,3-dihydroxypropyl)-6-fluoro-5-(2-fluoro-4-iodophenylamino)-8-methylpyrido [2,3-d] pyrimidine-4,7 (3H, 8H)-dione) or AZD-8330 (2-(2-fluoro-4-iodophenylamino)-N-(2-hydroxyethoxy)-1,5-dimethyl-6-oxo-1,6-dihydropyridine-3-carboxamide) and the like] and the like. Only one kind of the substance may be used or two or more kinds thereof may be used in combination. PD0325901, PD184352, PD98059, U0126, MEK162, SL327, TAK-733 and AZD-8330 are known MEK inhibitors, and a commercially available product and the like can be obtained as appropriate. As the MEK inhibitor, preferred is, for example, PD0325901, PD184352, U0126, TAK-733 or AZD-8330.

In the present invention, the concentration of the MEK inhibitor contained in the medium is not particularly limited as long as retinal pigment epithelial cells of mammals can be produced by the method of the present invention, and can be appropriately determined by those of ordinary skill in the art according to the kind of the MEK inhibitor. For example, the concentration of the MEK inhibitor is in a concentration range showing an MEK inhibitory activity corresponding to 0.001-10 µM, preferably 0.005-5 µM, more preferably 0.1-4 µM, more preferably 0.25-4 µM, particularly preferably 0.25-2 µM, of PD0325901. For example, a concentration range of 0.01-20 µM, preferably 0.1-10 µM, more preferably 1.5-6 µM, of PD184352 can be mentioned. The concentration may be constant through the first step or may be varied in steps as long as retinal pigment epithelial cells can be produced by the method of the present invention.

In the present invention, BMP receptor inhibitor is not particularly limited as long as it is a substance capable of suppressing signal transduction mediated by BMP, and may be any of protein, nucleic acid and low-molecular-weight compound. As the representative BMP, BMP2, BMP4, BMP7, GDF7 and the like can be mentioned. The BMP receptor (BMPR) here is present as a heterodimer of TYPE I receptor (ALK (activin receptor-like kinase)-1, ALK-2, ALK-3, ALK-6) and TYPE II receptor (ActRII, BMPRII). Examples of the BMP receptor inhibitor include, but are not limited to, a substance that directly acts on BMP or BMP receptor (e.g., antibody, aptamer etc.), a substance that suppresses expression of a gene encoding BMP or BMP receptor (e.g., antisense oligonucleotide, siRNA etc.), a substance that inhibits binding of BMP receptor and BMP (e.g., soluble BMP receptor, BMP antagonist etc.), a substance that inhibits physiological activity caused by signal transduction by BMP receptor [low-molecular-weight compounds such as LDN193189 (4-[6-(4-Piperazin-1-ylphenyl)pyrazolo[1,5-a]pyrimidin-3-yl]quinoline) or Dorsomorphin (6-[4-[2-(1-Piperidinyl)ethoxy]phenyl]-3-(4-pyridinyl)-pyrazolo[1,5-a]pyrimidine) and the like, and the like] and the like. Only one kind of the substance may be used or two or more kinds thereof may be used in combination. LDN193189 and Dorsomorphin are known BMP TYPE I receptor inhibitors, and a commercially available product and the like can be obtained as appropriate. As the BMP receptor inhibitor, preferred is, for example, LDN193189.

The Sonic hedgehog (hereinafter sometimes to be indicated as Shh) signal transduction pathway agonist in the present invention is not particularly limited as long as it is a substance capable of enhancing signal transduction mediated by Shh, and may be any of protein, nucleic acid and low-molecular-weight compound. Examples of the Shh signal transduction pathway agonist include, but are not limited to, proteins belonging to the Hedgehog family (e.g., Shh and Ihh), Shh receptor, Shh receptor agonist [low-molecular-weight compounds such as Purmorphamine (9-Cyclohexyl-N-[4-(4-morpholinyl)phenyl]-2-(1-naphthalenyloxy)-9H-purin-6-amine), or SAG (Smoothened Agonist; N-Methyl-N'-(3-pyridinylbenzyl)-N'-(3-chlorobenzo[b]thiophene-2-carbonyl)-1,4-diaminocyclohexane) and the like, and the like] and the like. Only one kind of the substance may be used or two or more kinds thereof may be used in combination. Purmorphamine and SAG are known Shh signal transduction pathway agonists, and a commercially available product and the like can be obtained as appropriate. As the Shh signal transduction pathway agonist, preferred is, for example, SAG.

In the present invention, PKC inhibitor is not particularly limited as long as it is a substance capable of inhibiting expression or activity of protein kinase C (PKC), and may be any of protein, nucleic acid and low-molecular-weight compound. PKC here is a protein family constituted of at least 10 kinds of isozymes, and the PKC inhibitor is a substance that inhibits the expression or activity of one, a plurality or all of these PKC families. Examples of the substance include, but are not limited to, a substance that suppresses expression of a gene encoding PKC (e.g., antisense oligonucleotide, siRNA etc.), a substance that inhibits enzyme activity of PKC [for example, low-molecular-weight compounds such as Go6983 (3-[1-[3-(Dimethylamino)propyl]-5-methoxy-1H-indol-3-yl]-4-(1H-indol-3-yl)-1H-pyrrole-2,5-dione) and the like, and the like] and the like. Only one kind of the substance may be used or two or more kinds thereof may be used in combination. Go6983 is a known PKC inhibitor, and a commercially available product and the like can be obtained as appropriate. As the PKC inhibitor, preferred is, for example, Go6983.

In the present invention, the concentration of the BMP receptor inhibitor, Sonic hedgehog signal transduction pathway agonist and PKC inhibitor contained in the medium can be appropriately determined by those of ordinary skill in the art to fall within a range capable of producing retinal pigment epithelial cells by the method of the present invention. For example, the concentration of the BMP receptor inhibitor is in a concentration range showing a BMP receptor inhibitory activity corresponding to 1-1000 nM, preferably 10-500 nM, more preferably 30-300 nM, of LDN193189. The concentration of the Shh signal transduction pathway agonist is in a concentration range showing an Shh signal transduction action corresponding to 1-2000 nM, preferably 3-1000 nM, more preferably 10-500 nM, of SAG. The concentration of the PKC inhibitor is a concentration range showing a PKC inhibitory activity corresponding to 0.05-20 $\mu$M, preferably 0.2-10 $\mu$M, more preferably 0.5-5 $\mu$M, of Go6983.

The concentration may be constant through the first step or may be varied in steps as long as retinal pigment epithelial cells can be produced by the method of the present invention.

In the first step, the pluripotent stem cells may be cultured under any conditions of suspension culturing and adhesion culturing, preferably adhesion culturing.

The culture vessel to be used for adhesion culturing pluripotent stem cells is not particularly limited as long as it enables adhesion culturing of cells. It is preferably a cell-adhesive culture vessel. As the cell-adhesive culture vessel, a culture vessel artificially treated to improve cell adhesiveness can be used, and specifically, the aforementioned culture vessel whose inside is coated with a coating agent can be mentioned. Examples of a preferable coating agent include extracellular matrix such as laminin [including laminin $\alpha5\beta1\gamma1$ (laminin 511), laminin $\alpha1\beta1\gamma1$ (laminin 111) and the like and laminin fragment (laminin 511E8 etc.)], entactin, collagen, gelatin, vitronectin, Synthemax (Corning Incorporated), Matrigel and the like, and the like or polymers such as polylysine, polyornithine and the like, and the like, with laminin 511E8 being more preferred (WO 2015/053375). Laminin 511E8 can be a commercially available product (e.g., iMatrix-511, Nippi).

The culture vessel to be used for suspension culturing pluripotent stem cells is not particularly limited as long as it enables culturing of cells in suspension. It is preferably non-cell-adhesive.

The culture conditions such as culture temperature, and $CO_2$ concentration in the first step can be appropriately determined. While the culture temperature is not particularly limited, it is, for example, about 30° C. to 40° C., preferably about 37° C. The $CO_2$ concentration is, for example, about 1% to about 10%, preferably about 5%.

The medium can be exchanged in the middle of the first step. The method of medium exchange is not particularly limited, and the whole amount of the original medium may be exchanged with a fresh medium or only a part of the original medium may be exchanged with a fresh medium. When a part of the original medium is exchanged with a fresh medium, the final concentrations of the substances (MEK inhibitor, FGF receptor inhibitor etc.) contained in the first step are first calculated, and then a fresh medium containing the substances at concentrations corresponding to the ratio of the medium to be exchanged is prepared and exchanged with the medium. The final concentrations of the substances contained in the first step may be changed during the culturing.

While the tool used for the medium exchange operation is not particularly limited, for example, pipetter, micropipette, multichannel micropipette, continuous dispenser, and the like can be mentioned. For example, when a 96 well plate is used as a culture vessel, a multi-channel Pipetman may be used.

The number of days of the first step is not particularly limited as long as it is within the period when the cells produced by exposure of pluripotent stem cells to the above-mentioned FGF receptor inhibitor and/or MEK inhibitor and the like maintain differentiation potency into retinal pigment epithelial cells. The pluripotent stem cells in the first step are cultured for a period not exceeding 30 days. The period may vary according to the line of the pluripotent stem cells to be used and the like. It is generally not less than 2 days, preferably not less than 3 days, more preferably not less than 4 days. In the first step, pluripotent stem cells are more preferably cultured for 2 days-13 days or 2 days-6 days, further preferably 4 days-6 days.

The number of days of the first step may also be determined using, as an index, a particular marker expressed in the pluripotent stem cells treated with the above-mentioned FGF receptor inhibitor and/or MEK inhibitor. Specifically, for example, the culturing of the first step is performed for a period sufficient to induce expression of markers in the early stage of eye formation such as PAX6 (Paired box protein 6), LHX2 (LIM homeobox 2) and SIX3 (SIX homeobox 3) and the like, specifically, at least one gene of the eye field transcription factors, and then the second step can be performed. That is, examples of the "period not exceeding 30 days" in the first step include "a period sufficient for inducing expression of at least one marker in the early stage of eye formation, specifically, eye field transcription factor and of not more than 30 days" and "a period sufficient for inducing gene expression of at least one of PAX6, LHX2 and SIX3 and of not more than 30 days". In these embodiments, the upper limit of the culture period is, for example, a period not exceeding 30 days, a period not exceeding 13 days, or a period not exceeding 6 days or the like.

Whether a given culture period under given culture conditions is "a period sufficient for inducing expression of at least one marker in the early stage of eye formation, specifically, eye field transcription factor" or "a period sufficient for inducing gene expression of at least one of PAX6, LHX2 and SIX3" can be determined by confirming whether expression of at least one of these genes can be significantly detected as compared to the untreated control, in a cell population after culturing for the period under the conditions. Those of ordinary skill in the art can detect expression of these genes by a method such as Northern blot, RT-PCR, microarray and the like.

PAX6, LHX2 and SIX3 are genes encoding an eye field transcription factor expressed in the eye field region in an early developmental stage and respectively specified as Genbank Accession No.: NM_001127612, Genbank Accession No.: NM_004789, Genbank Accession No.: NM_005413 as human genes. These genes in other animal species such as mouse and the like can be easily specified by those of ordinary skill in the art, and can be specified from, for example, base sequences of genes recited in http://www.ncbi.nlm.nih.gov.

That is, in one embodiment of the present invention, a production method of retinal pigment epithelial cells including the following steps is provided.
(1) a first step for culturing a pluripotent stem cell in a medium comprising an FGF receptor inhibitor and/or an MEK inhibitor for a period sufficient for inducing gene expression of at least one eye field transcription factor, and
(2) a second step for culturing the cell obtained in the first step in the presence of a Nodal signal transduction pathway inhibitor and/or a Wnt signal transduction pathway inhibitor to form a retinal pigment epithelial cell.

That is, in another embodiment of the present invention, a production method of retinal pigment epithelial cells including the following steps is provided.
(1) a first step for culturing a pluripotent stem cell in a medium comprising an FGF receptor inhibitor and/or an MEK inhibitor for a period sufficient for inducing gene expression of at least one of PAX6, LHX2 and SIX3, and
(2) a second step for culturing the cell obtained in the first step in the presence of a Nodal signal transduction pathway inhibitor and/or a Wnt signal transduction pathway inhibitor to form a retinal pigment epithelial cell.

When the first step is performed by adhesion culture, cells can also be recovered by dissociating the cells from the culture vessel.

A method for dissociating the cells from the culture vessel is not particularly limited as long as it is generally known as a method for dissociating cells. A cell dissociation solution containing enzyme such as trypsin and the like can be used. Also, a commercially available cell dissociation solution [TrypLE select (Life Technologies) and the like] can also be used. The dissociated and recovered cells are generally washed with PBS (Phosphate Buffered Saline) and/or a medium used in the second step, and then used in the second step.

The cells obtained in the first step can be passaged (maintenance culture), stored as an intermediate for production of retinal pigment epithelial cells, or subjected to other treatment as long as their differentiation state and survival state are maintained. A method for cryopreserving the cells obtained in the first step is not particularly limited as long as it is generally known as a method for cryopreserving cells. For example, the cells obtained in the first step may be suspended in a medium containing a cryoprotective agent such as DMSO or glycerin and the like and cryopreserved.

In addition, a commercially available cell cryopreservation solution [StemCellBanker (Zenoaq)] can also be used.

(2) The Second Step

The second step in which the cells obtained in the first step are cultured in the presence of a Nodal signal transduction pathway inhibitor and/or a Wnt signal transduction pathway inhibitor to form a retinal pigment epithelial cell is explained below.

The concentration of the cells when the second step is started can be appropriately set by those of ordinary skill in the art. It is, for example, $1.0 \times 10^2$ cells/cm$^2$ to $2 \times 10^6$ cells/cm$^2$, preferably $3 \times 10^2$ cells/cm$^2$ to $1 \times 10^6$ cells/cm$^2$, more preferably $1 \times 10^3$ cells/cm$^2$ to $2 \times 10^3$ cells/cm$^2$, further preferably $2 \times 10^3$ to cells/cm$^2$ to $4 \times 10^4$ cells/cm$^2$, in the case of adhesion culture.

The medium to be used in the second step is not particularly limited as long as it is as described in the above-mentioned section of definition. The medium to be used in the second step may be a serum-containing medium or serum-free medium. To avoid contamination of chemically-undefined components, a serum-free medium is preferably used in the present invention. To avoid complicated preparation, for example, a serum-free medium supplemented with an appropriate amount of a commercially available serum replacement such as KSR and so on (e.g., Glasgow MEM medium supplemented with KSR at a concentration range of 0.5% to 30%) can be used.

The medium to be used in the second step may optionally contain a ROCK (Rho-associated coiled-coil forming kinase/Rho-associated kinase) inhibitor to suppress cell death (apoptosis). As the ROCK inhibitor, Y-27632, Fasudil or H-1152 can be mentioned. The concentration of the ROCK inhibitor can be appropriately set by those of ordinary skill in the art. For example, it can be set within the concentration range showing a ROCK inhibitory activity corresponding to about 50 nM-200 μM of Y-27632.

In the method of the present invention, the Nodal signal transduction pathway inhibitor is not particularly limited as long as it can suppress signal transduction mediated by Nodal, and may be any of protein, nucleic acid and low-molecular-weight compound. The signal mediated by Nodal is transduced via a Nodal receptor. The Nodal receptor is present as a heterodimer of TYPE I receptor (ALK (activin receptor-like kinase)-4, ALK-5, ALK-7) and TYPE II receptor (ActRII). Examples of the Nodal signal transduction pathway inhibitor include, but are not limited to, a substance that directly acts on Nodal or Nodal receptor (anti-Nodal antibody, anti-Nodal receptor antibody etc.), a substance that suppresses expression of a gene encoding Nodal or Nodal receptor (e.g., antisense oligonucleotide, siRNA etc.), a substance that inhibits binding of Nodal receptor and Nodal (Lefty-A, Lefty-B, Lefty-1, Lefty-2, soluble Nodal receptor etc.), a substance that inhibits physiological activity caused by signal transduction by Nodal receptor [low-molecular-weight compounds such as SB-431542 (SB431542) (4-[4-(1,3-Benzodioxol-5-yl)-5-(pyridin-2-yl)-1H-imidazol-2-yl]benzamide) that inhibits kinase activity of TYPE I receptor by ATP competition and the like, and the like] and the like. SB-431542 is a known Nodal signal inhibitor and is appropriately available as a commercially available product and the like. As the Nodal signal inhibitor, preferred is, for example, SB-431542.

In the method of the present invention, the Wnt signal transduction pathway inhibitor is not particularly limited as long as it can suppress signal transduction mediated by Wnt, and may be any of protein, nucleic acid, low-molecular-weight compound and the like. The signal mediated by Wnt is transduced via a Wnt receptor present as a heterodimer of Frizzled (Fz) and LRP5/6 (low-density lipoprotein receptor-related protein 5/6). Examples of the Wnt signal transduction pathway inhibitor include, but are not limited to, a substance that directly acts on Wnt or Wnt receptor (anti-Wnt antibody, anti-Wnt receptor antibody etc.), a substance that suppresses expression of gene encoding Wnt or Wnt receptor (e.g., antisense oligonucleotide, siRNA etc.), a substance that inhibits binding of Wnt receptor and Wnt (soluble Wnt receptor, dominant negative Wnt receptor etc., Wnt antagonist, Dkk1, Cerberus protein etc.), a substance that inhibits physiological activity caused by signal transduction by Wnt receptor [low-molecular-weight compounds such as casein kinase I inhibitors CKI-7 (N-(2-Aminoethyl)-5-chloroisoquinoline-8-sulfonamide) and D4476 (4-[4-(2,3-Dihydro-1,4-benzodioxin-6-yl)-5-(2-pyridinyl)-1H-imidazol-2-yl]benzamide), IWR-1-endo (IWR1e) (4-[(3aR,4S,7R,7aS)-1,3,3a,4,7,7a-hexahydro-1,3-dioxo-4,7-methano-2H-isoindol-2-yl]-N-8-quinolinyl-benzamide) that stabilizes β-catenin destruction complex by inhibiting metabolic turnover of Axin, and IWP-2 (N-(6-Methyl-2-benzothiazolyl)-2-[(3,4,6,7-tetrahydro-4-oxo-3-phenylthieno[3,2-d]pyrimidin-2-yl)thio]acetamide) that inactivates Porcupine (Porcn) as a membrane-bound O-acyltransferase (MBOAT) and suppresses palmitoylation of Wnt protein and the like, and the like] and the like. CKI-7, D4476, IWR-1-endo (IWR1e), IWP-2 and the like are known Wnt signal inhibitors, and commercially available products and the like are available as appropriate. A preferable Wnt signal inhibitor is CKI-7.

In the second step, Nodal signal transduction pathway inhibitor or Wnt signal transduction pathway inhibitor can be used singly but preferably, they are used in combination.

In the present invention, the concentrations of the Nodal signal transduction pathway inhibitor and Wnt signal transduction pathway inhibitor contained in the medium can be appropriately determined by those of ordinary skill in the art to fall within a range capable of producing retinal pigment epithelial cells by the method of the present invention. For example, when SB-431542 is used as the Nodal signal transduction pathway inhibitor, the concentration thereof is generally 0.01-50 μM, preferably 0.1-10 μM, more preferably 5 μM; when CKI-7 is used as the Wnt signal transduction pathway inhibitor, the concentration thereof is generally 0.01-30 μM, preferably 0.1-30 μM, more preferably 3 μM.

The concentration may be constant through the second step or may be varied in steps as long as retinal pigment epithelial cells can be produced by the method of the present invention.

The culturing in the second step may be performed under any conditions of suspension culturing and adhesion culturing, preferably adhesion culturing.

While a culture vessel used for adhesion culturing in the second step is not particularly limited as long as adhesion culturing of cells can be performed, a cell-adhesive culture vessel is preferable. As the cell-adhesive culture vessel, culture vessels artificially treated to improve cell adhesiveness can be used, and specifically, the above-mentioned culture vessel whose inside is coated with a coating agent can be mentioned. Preferable examples of the coating agent include extracellular matrix such as laminin [including laminin α5β1γ1 (laminin 511), laminin α1β1γ1 (laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like, and the like. More preferred is laminin 511E8 (WO 2015/053375). As laminin 511E8, a commercially available product (e.g., iMatrix-511, Nippi) can be used.

The culture vessel to be used for suspension culturing in the second step is not particularly limited as long as it enables culturing of cells in suspension. It is preferably non-cell-adhesive.

The culture conditions such as culture temperature, $CO_2$ concentration and so on in the second step can be appropriately determined. The culture temperature is, for example, about 30° C. to about 40° C., preferably about 37° C. The $CO_2$ concentration is, for example, about 1% to about 10%, preferably about 5%.

The medium can be exchanged as appropriate in the middle of the second step. The method of medium exchange is not particularly limited, and the whole amount of the original medium may be exchanged with a fresh medium or only a part of the original medium may be exchanged with a fresh medium. When a part of the original medium is exchanged with a fresh medium, the final concentrations of the substances (Nodal signal transduction pathway inhibitor, Wnt signal transduction pathway inhibitor, KSR etc.) contained in the second step are first calculated, and then a fresh medium containing the substances at concentrations corresponding to the ratio of the medium to be exchanged may be prepared and exchanged with the medium. The final concentrations of the substances contained in the second step may be changed during the culturing.

While the tool used for the medium change operation is not particularly limited, for example, pipetter, micropipette, multichannel micropipette, continuous dispenser, and the like can be mentioned. For example, when a 96 well plate is used as a culture vessel, a multichannel pipette may be used.

A culture period of the second step is not particularly limited as long as it is a period capable of inducing retinal pigment epithelial cells of interest. As an example of such culture period, retinal pigment epithelial cells can be produced generally on days 14-40 calculating from the start of the second step.

Those of ordinary skill in the art can confirm the generation of retinal pigment epithelial cells based on the expression of a cell marker (RPE65 (retinal pigment epithelial cells), Mitf (retinal pigment epithelial cells) BEST1 (retinal pigment epithelial cells), CRALBP (retinal pigment epithelial cells) and the like), presence of melanin granules (brown-black), intercellular tight junction, characteristic polygonal or cobblestone-like cell morphology and the like, and the culture period can also be determined by confirming them.

After the completion of the second step, it is preferable to exchange the medium with a maintenance medium for retinal pigment epithelial cells (hereinafter sometimes to be indicated as RPE maintenance medium) and further culture same. As a result, a melanin dye-deposited cell population and a polygonal flat cell population adhered to the basal lamina can be observed more clearly. Culturing in an RPE maintenance medium is not limited as long as a colony of retinal pigment epithelial cells can be formed. For example, the cells are further cultured for about 5-20 days while exchanging the total amount of the medium is exchanged at a frequency of not less than once in 3 days.

As the maintenance medium for retinal piyiuent epithelial cells, for example, those described in IOVS, March 2004, Vol. 45, No. 3, Masatoshi Haruta, et. al., IOVS, November 2011, Vol. 52, No. 12, Okamoto and Takahashi, J. Cell Science 122 (17), Fumitaka Osakada, et. al., IOVS, February 2008, Vol. 49, No. 2, Gamm, et. al. can be used, which are constituted of a basal medium, a serum and/or a serum replacement, and other components.

The basal medium is not particularly limited as long as it is as described in the above-mentioned section of definition. As the serum, a serum derived from a mammal such as bovine, human and the like can be used. In the present invention, a serum replacement is preferably used, and B27, which is a serum replacement for nerve cells, is particularly preferable from the aspect of quality management of the cell of interest. Examples of other components include L-glutamine, penicillin sodium, streptomycin sulfate and the like.

A highly pure retinal pigment epithelial cell can be obtained by a concentration or purification operation after completion of the second step. The concentration or purification method is not particularly limited as long as it is generally known as a method of concentrating/purifying cells and, for example, methods such as filtration (e.g., WO 2015/053376), centrifugation, perfusion separation, flow cytometry separation, trap separation by antibody immobilized carrier and the like can be used.

The production method of the present invention may contain a step for amplifying retinal pigment epithelial cells after completion of the second step. For example, retinal pigment epithelial cells can be expanded by the method described in WO 2015/053375. According to the expansion method described in WO 2015/053375, cells insufficient in the differentiation induction which is contained in the cultured cells and the like can be eliminated by selection, and byproducts other than the retinal pigment epithelial cells can be relatively decreased. Therefore, the expansion step can also be a purification step of the retinal pigment epithelial cells.

When retinal pigment epithelial cells are produced by suspension culture in the second step, the retinal pigment epithelial cells can be recovered as single cells and can be utilized after preparing as a suspension.

When retinal pigment epithelial cells are produced by adhesion culture in the second step, the retinal pigment epithelial cells can be adhered to each other to form a sheet-like structure. Therefore, a sheet of retinal pigment epithelial cells that can be transplanted to patients can be produced. The sheet of retinal pigment epithelial cells is particularly useful as a cell population to be used as a cell transplantation therapeutic drug for the treatment of retinal diseases. It is also possible to dissociate the retinal pigment epithelial cells produced by adhesion culture by the above-mentioned method, recover the retinal pigment epithelial cells as independent single cells, and suspend them in a physiological aqueous solvent (saline, buffer, serum-free medium etc.) to give a suspension.

3. Toxicity, Efficacy Evaluation Method

The retinal pigment epithelial cells produced by the production method of the present invention can be utilized as a normal or disease model cell for screening for and efficacy evaluation of therapeutic drugs for retinal diseases and therapeutic drug for diseases of other complications such as diabetes and the like, or prophylactic drug thereof, safety test of chemical substances and the like, stress test, toxicity test, side effect test, infection/contamination test. On the other hand, they can also be utilized for toxicity study, toxicity test and the like of phototoxicity unique to retinal cells, retinal excitotoxicity and the like. The evaluation method thereof includes stimulation and toxicity tests such as apoptosis evaluation and the like, as well as tests for evaluation of influence on normal differentiation from progenitor cell into retinal pigment epithelial cell and photoreceptor (RT-PCR of various gene markers, analysis of protein expression by ELISA of cytokine, phagocytic capacity test and the like), toxicity test of phototoxicity and the like, retinal electric potential and transepithelial impedance on visual function, cytotoxicity test caused by autoimmune reaction and the like. As a cell material for these tests, not only retinal pigment epithelial cells but also progenitor cells thereof can be used and, for example, a plate on which cells are adhered by seeding, a cell suspension, a sheet or compact thereof can be provided. They can be used as an extrapolation test of human and animal tests.

4. Pharmaceutical Composition

The present invention provides a pharmaceutical composition containing an effective amount of retinal pigment epithelial cells produced by the production method of the present invention.

The pharmaceutical composition contains an effective amount of retinal pigment epithelial cells produced by the production method of the present invention and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending retinal pigment epithelial cells produced by the production method of the present invention in an appropriate physiological aqueous solvent. Where necessary, the composition may be added with a cryopreservative, cryopreserved with liquid nitrogen and the like, thawed when in use, washed with buffer, and used for a transplantation therapy.

The retinal pigment epithelial cells obtained by the production method of the present invention may also be cut in an appropriate size with tweezers and the like to give a sheet preparation.

Cells obtained by the production method of the present invention may also be subjected to adhesion culturing in the second step for differentiation induction to give cells in the form of a sheet to provide a sheet preparation.

The pharmaceutical composition of the present invention is useful as a therapeutic drug for a disease based on (caused by) a disorder of retinal pigment epithelial cells.

5. Therapeutic Drug and Treatment Method for Retinal Diseases

The retinal pigment epithelial cells (including retinal pigment epithelial cells that underwent the above-mentioned concentration and amplification operation and the like) produced by the production method of the present invention can be used as a cell transplantation therapeutic drug to be transplanted in the form of a suspension or sheet to living organisms for the treatment of retinal diseases. The present invention also provides a treatment method comprising administering the therapeutic drug to patients. Retinal disease here is an ophthalmic disease relating to the retina and also includes complications with other diseases such as diabetes and the like. The retinal disease in the present invention includes, for example, diseases based on disorders of retinal pigment epithelial cells, such as age-related macular degeneration, retinal pigment denaturation, diabetic retinopathy or retinal detachment and the like. That is, the retinal pigment epithelial cells produced by the production method of the present invention can be used for supplementing the damaged site of retinal pigment epithelial cells in patients.

In transplantation therapy, rejection due to the difference in histocompatibility antigens often poses a problem. The problem can be solved by using pluripotent stem cells (e.g., induced pluripotent stem cells) established from the somatic cell of others who are immunologically compatible with the recipient (e.g., compatible in part or all of HLA type and MHC type), or pluripotent stem cells (e.g., induced pluripotent stem cells) established from the somatic cells of the transplantation recipient.

That is, in a preferable embodiment, as pluripotent stem cells in the method of the present invention, allogenic retinal pigment epithelial cells or tissues containing same are produced from the pluripotent stem cells established from the somatic cells of other people whose immunity is compatible with that of the recipient, and they are transplanted to the recipient. Alternatively, pluripotent stem cells (e.g., induced pluripotent stem cells) established from the somatic cells of the recipient are used to produce a retinal pigment epithelial cell, which is immunologically self for the recipient, or a tissue containing same and it is transplanted to the recipient.

All reference documents cited in the present specification, including publications, patent documents, description of patent applications and the like, are hereby incorporated in their entireties by reference, to the extent that they have been disclosed herein.

EXAMPLES

The present invention is explained in detail in the following by referring to Examples, which are not to be construed as limited thereto.

In the following Examples and Comparative Examples, iPS cell (201B7, Kyoto University) derived from human dermal fibroblast, and iPS cells (1231A3, Ff-I01, QHJI01) derived from mononuclear cells derived from human peripheral blood established by Kyoto University from ePBMC® of Cellular Technology Limited were used.

Example 1: Highly Efficient Production of Retinal Pigment Epithelial Cells Including MEK Inhibitor Treatment Step and Using Human iPS Cell Culture for maintaining undifferentiated state of human iPS cells (201B7 line and 1231A3 line) under feeder-free conditions was performed according to the method described in "Nakagawa, M. et. al., Sci. Rep. 2014 Jan. 8; 4: 3594". The medium used was StemFit® AK03 medium (Ajinomoto Co., Inc.) (hereinafter AK03 medium) or Essential 8 medium (Life Technologies).

Production of retinal pigment epithelial (RPE) cells including an MEK inhibitor treatment step was performed as follows. iPS cells under culture for maintaining undifferentiated state were treated with 0.5×TrypLE select (mixture of equal amounts of TrypLE select (Life Technologies)) and 0.5 mM EDTA/PBS(−)), dissociated using a cell scraper, dispersed to single cells by pipetting, seeded in a 6-well culture plate coated with iMatrix-511 (Nippi) (0.5 µg/cm$^2$) at $1.2 \times 10^4$ cells per 1 well, and cultured in an AK03 medium or Essential 8 medium containing a ROCK inhibitor [10 µM Y-27632 (Wako Pure Chemical Industries, Ltd.)] under 37° C., 5% $00_2$ conditions. On the next day of seeding, PD0325901 (SIGMA) as an MEK inhibitor was added to the AK03 medium at a final concentration of 1 µM or Essential 8 medium at a final concentration of 0.03 µM (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 µg/cm$^2$) at $2.0 \times 10^5$ cells per 1 well when AK03 medium was used and at $5.0 \times 10^5$ cells when Essential medium was used, and cultured under 37° C., 5% $CO_2$ conditions (start of the second step). On the first day of culture, AK03 medium or Essential 8 medium added with Y-27632 (final concentration 10 µM), SB-431542 (Wako Pure Chemical Industries, Ltd.) (final concentration 5 µM) as Nodal signal transduction pathway inhibitor, and CKI-7 (SIGMA) (final concentration 3 µM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration µM), SB-431542 (final concentration 5 µM) and CKI-7 (final concentration 3 µM) was used; from 6 to 9 days of culture, the basal medium added with 15% KSR, Y-27632 (final concentration µM), SB-431542 (final concentration 5 µM), CKI-7 (final concentration 3 µM) was used; from 10 to 13 days of culture, the basal medium added with 10% KSR, Y-27632 (final concentration 10 µM), SB-431542 (final concentration 5 µM), CKI-7 (final concentration 3 µM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-supplement (Life Technologies), 1.9 mM L-glutamine, 96 U/ml penicillin-96 µg/ml streptomycin] was used. The whole amount of the medium was exchanged every day.

Figure 2:
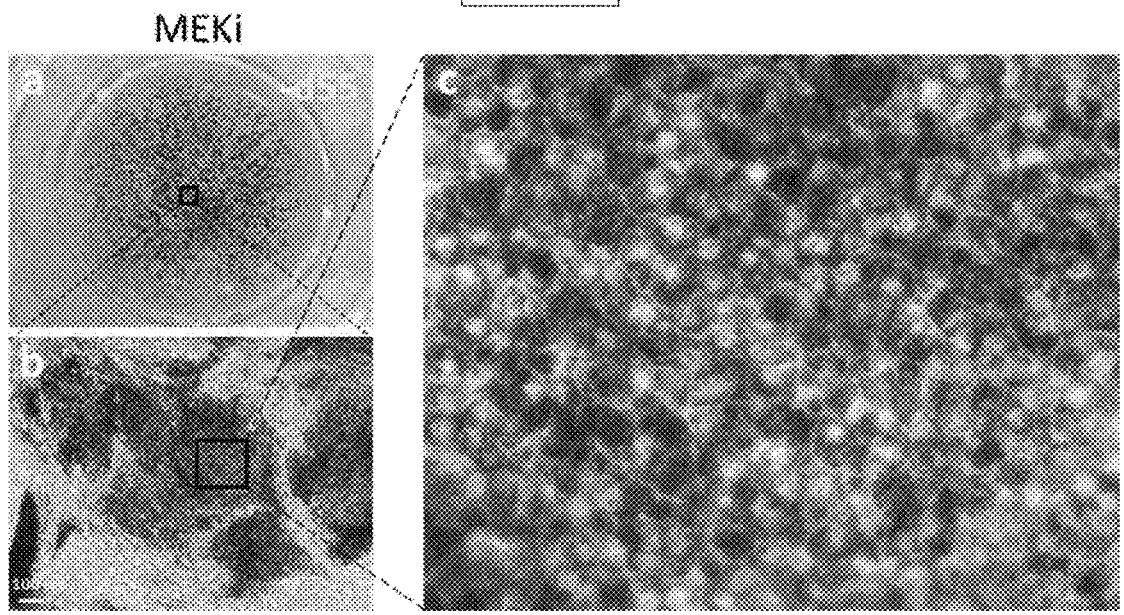
FIG. 2 shows (a) photograph, (b) low magnification phase contrast microscopic image and (c) high magnification bright field microscopic image of a 6-well culture plate after 55 days of culture containing iPS cell (201B7)-derived RPE cells produced by a production method comprising an MEK inhibitor treatment step. MEKi: MEK inhibitor (1 µM PD0325901).

The culture plate was observed from 38 to 42 days of culture. As a result, when the both media of AK03 medium and Essential 8 medium were used, emergence of a brown-black cell population could be confirmed over a wide area in the both lines of 201B7 line and 1231A3 line (FIG. 1). By microscopic observation, the cells showed typical characteristics of RPE cell such as a brown-black, polygonal, cobblestone-like morphology (FIG. 2).

Comparative Example 1: Production of Retinal Pigment Epithelial Cells not Including MEK Inhibitor Treatment Step and Using Human iPS Cell Culture for maintaining undifferentiated state of human iPS cells (201B7 line and 1231A3 line) under feeder-free conditions was performed according to the method described in "Nakagawa, M. et. al., Sci. Rep. 2014 Jan. 8; 4: 3594". The medium used was "StemFit®" AK03 medium (Ajinomoto Co., Inc.) (hereinafter AK03 medium) or Essential 8 medium (Life Technologies).

Production of retinal pigment epithelial (RPE) cells not including an MEK inhibitor treatment step was performed as follows. iPS cells under for maintaining undifferentiated state were treated with 0.5×TrypLE select, dissociated using a cell scraper, dispersed to single cells by pipetting, seeded in a 6-well culture plate coated with iMatrix-511 (Nippi) (0.5 µg/cm$^2$) at $2.0 \times 10^5$ cells per 1 well when AK03 medium was used and at $5.0 \times 10^5$ cells when Essential 8 medium was used, and cultured under 37° C., 5% $CO_2$ conditions. On the first day of culture, AK03 medium or Essential 8 medium added with Y-27632 (Wako Pure Chemical. Industries, Ltd.) (final concentration 10 μM) as a ROCK inhibitor, SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration 10 μM), SB-431542 (final concentration 5 μM) and CKI-7 (final concentration 3 μM) was used; from 6 to 9 days of culture, the basal medium added with 15% KSR, Y-27632 (final concentration 10 μM), SE-431542 (final concentration 5 μM), CKI-7 (final concentration 3 μM) was used; from 10 to 13 days of culture, the basal medium added with 10% KSR, Y-27632 (final concentration 10 μM), SE-431542 (final concentration 5 μM), CKI-7 (final concentration 3 μM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 μg/ml streptomycin] was used. The whole amount of the medium was exchanged every day.

Figure 3:
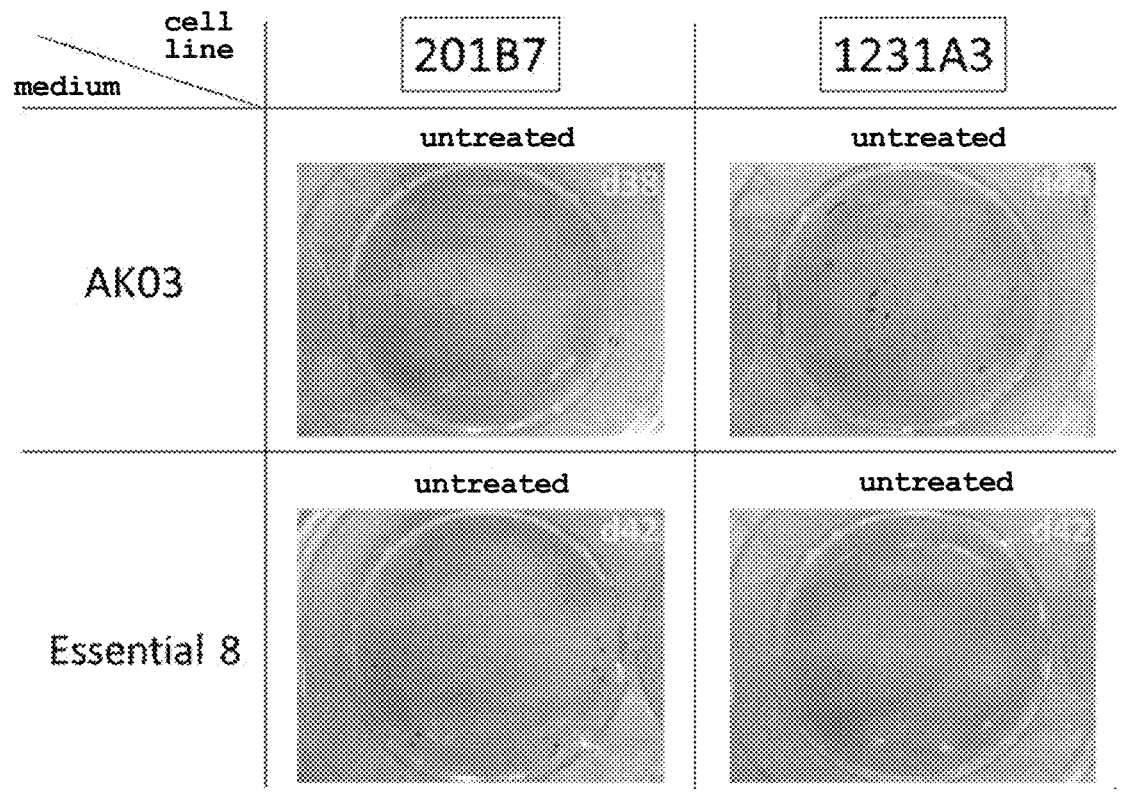
FIG. 3 shows photographs of 6-well culture plates after 38-42 days of culture containing iPS cell (201B7 or 1231A3)-derived differentiated cells produced by a production method without an MEK inhibitor treatment step using "StemFit®" AK03 medium or Essential 8 medium.

The culture plate was observed from 38 to 42 days of culture. As a result, only a few cells could be confirmed to show typical characteristics of RPE cell such as a brown-black, polygonal, cobblestone-like morphology (FIG. 3).

Example 2: Highly Efficient Production of Retinal Pigment Epithelial Cells Including FGF Receptor Inhibitor Treatment Step and Using Human iPS Cell Culture for maintaining undifferentiated state of human iPS cells (201B7 line and 1231A3 line) under feeder-free conditions was performed according to the method described in "Nakagawa, M. et. al., Sci. Rep. 2014 Jan. 8; 4: 3594". The medium used was "StemFit®" AK03 medium (Ajinomoto Co., Inc.) (hereinafter AK03 medium) or Essential 8 medium (Life Technologies).

Production of retinal pigment epithelial (RPE) cells including an FGF receptor inhibitor treatment step was performed as follows. iPS cells under culture for maintaining undifferentiated state were treated with 0.5×TrypLE select (mixture of equal amounts of TrypLE select (Life Technologies)) and 0.5 mM EDTA/PBS(−)), dissociated using a cell scraper, dispersed to single cells by pipetting, seeded in a 6-well culture plate coated with iMatrix-511 (Nippi) (0.5 μg/cm$^2$) at 1.2×10$^4$ cells per 1 well, and cultured in an AK03 medium or Essential 8 medium containing a ROCK inhibitor [10 μM Y-27632 (Wako Pure Chemical Industries, Ltd.)] under 37° C., 5% $CO_2$ conditions. On the next day of seeding, PD173074 (SIGMA) as an FGF receptor inhibitor was added to the AK03 medium or Essential 8 medium at a final concentration of 100 nM (start of the first step), and the cells were exposed thereto for 6 days (completion of the first step). In one embodiment, to study the effect of the FGF receptor inhibitor in a medium free of a factor for maintaining undifferentiated state (bFGF), StemSure hPSC Medium Δ (Wako Pure Chemical Industries, Ltd.) (hereinafter StemSure hPSC Medium Δ w/o bFGF) not added with bFGF was used. That is, PD173074 (SIGMA) as an FGF receptor inhibitor was added to StemSure hPSC Medium Δ w/o bFGF at a final concentration of 100 nM (start of the first step), and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 μg/cm$^2$) at 2.0×10$^5$ cells per 1 well when AK03 medium or StemSure hPSC Medium Δ w/o bFGF was used and at 5.0×10$^5$ cells when Essential 8 medium was used, and cultured under 37° C., 5% $CO_2$ conditions (start of the second step). On the first day of culture, AK03 medium, Essential 8 medium or StemSure hPSC Medium Δ w/o bFGF added with Y-27632 (Wako Pure Chemical Industries, Ltd.) (final concentration 10 μM) as a ROCK inhibitor, SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration 10 μM), SB-431542 (final concentration 5 μM) and CKI-7 (final concentration 3 μM) was used; from 6 to 9 days of culture, the basal medium added with 15% KSR, Y-27632 (final concentration 10 μM), SB-431542 (final concentration 5 μM), CKI-7 (final concentration 3 μM) was used; from 10 to 13 days of culture, the basal medium added with 10% KSR, Y-27632 (final concentration 10 μM), SB-431542 (final concentration 5 μM), CKI-7 (final concentration 3 μM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 μg/ml streptomycin] was used. The whole amount of the medium was exchanged every day.

Figure 4:
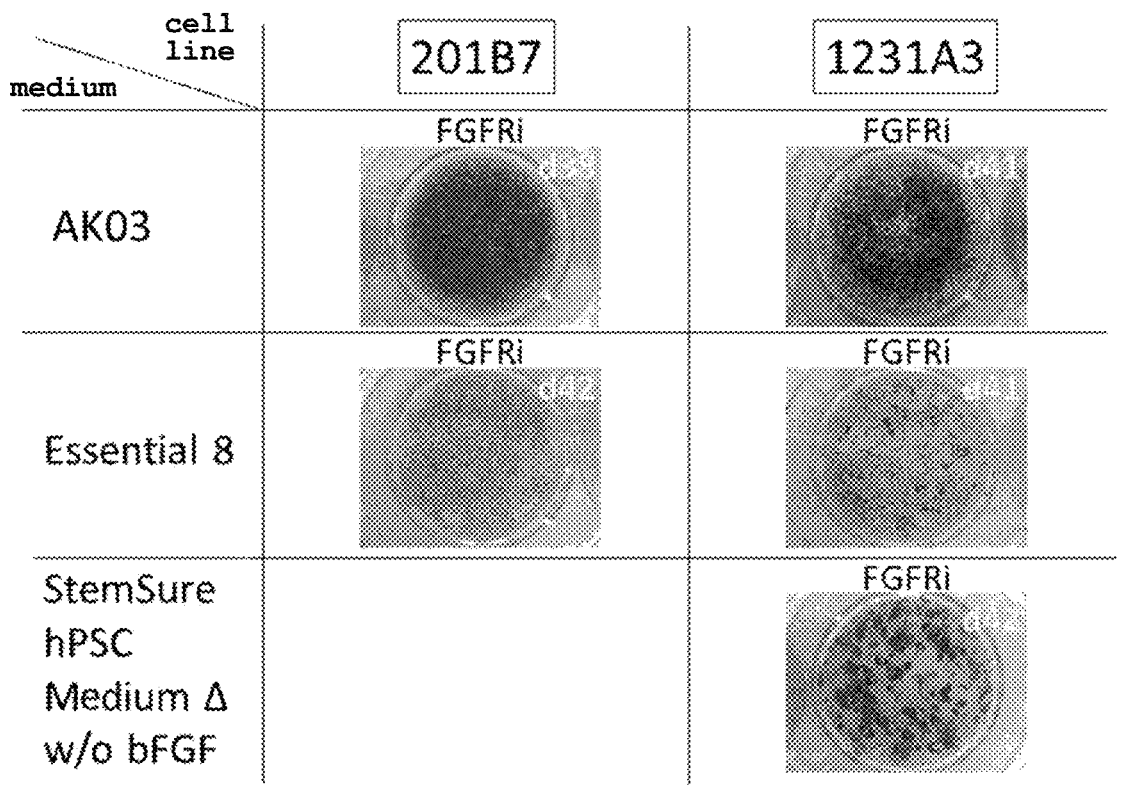
FIG. 4 shows photographs of 6-well culture plates after 38-42 days of culture containing iPS cell (201B7 or 1231A3)-derived retinal pigment epithelial (RPE) cells produced by a production method comprising an FGF receptor inhibitor treatment step using "StemFit®" AK03 medium, Essential 8 medium or StemSure hPSC Medium w/o bFGF. FGFRi: FGF receptor inhibitor (100 nM PD173074).
Figure 5:
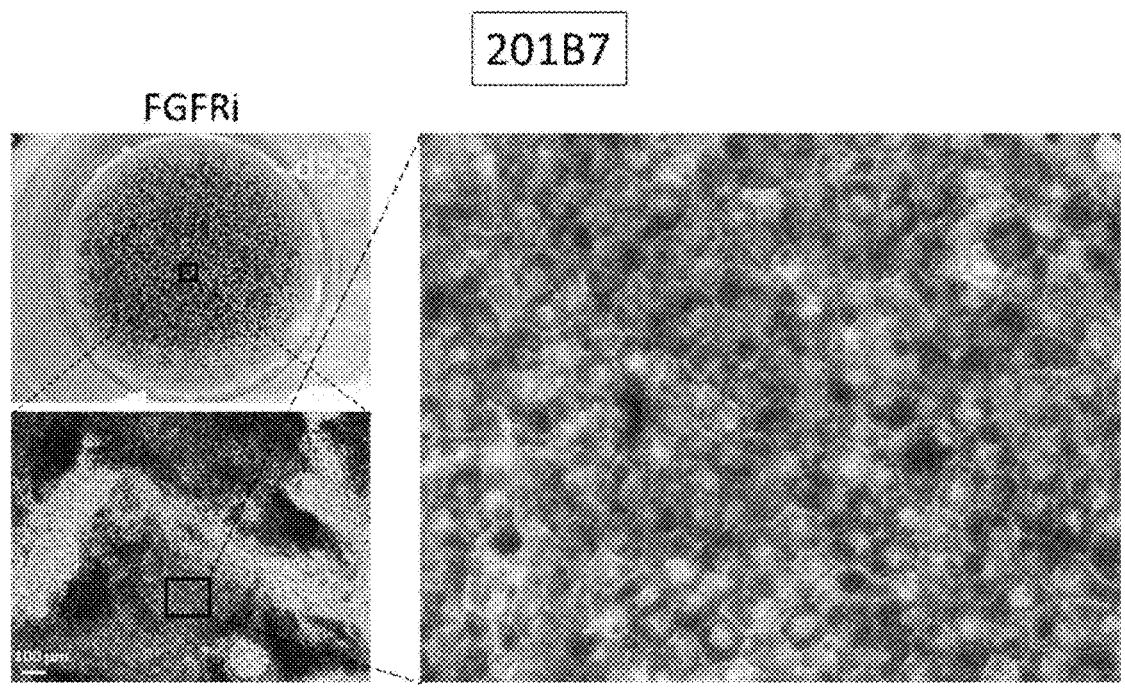
FIG. 5 shows (a) photograph, (b) low magnification phase contrast microscopic image and (c) high magnification bright field microscopic image of a 6-well culture plate after 55 days of culture containing iPS cell (201B7)-derived RPE cells produced by a production method comprising an FGF receptor inhibitor treatment step. FGFRi: FGF receptor inhibitor (100 nM PD173074).

The culture plate was observed from 38 to 42 days of culture. As a result, when the AK03 medium, Essential 8 medium or StemSure hPSC Medium Δ w/o bFGF was used, emergence of a brown-black cell population could be confirmed over a wide area in 201B7 line and/or 1231A3 line (FIG. 4). By microscopic observation, the cells showed typical characteristics of RPE cell such as a brown-black, polygonal, cobblestone-like morphology (FIG. 5).

Comparative Example 2: Production of Retinal Pigment Epithelial Cells not Including FGF Receptor Inhibitor Treatment Step and Using Human iPS Cell Culture for maintaining undifferentiated state of human iPS cells (201B7 line and 1231A3 line) under feeder-free conditions was performed according to the method described in "Nakagawa, M. et. al., Sci. Rep. 2014 Jan. 8; 4: 3594". "StemFit®" AK03 medium (Ajinomoto Co., Inc.) (hereinafter AK03 medium) or Essential 8 medium (Life Technologies) was used.

Production of retinal pigment epithelial (RPE) cells not including an FGF receptor inhibitor treatment step was performed as follows. iPS cells under culture for maintaining undifferentiated state or iPS cells cultured in StemSure hPSC Medium Δ w/o bFGF (Wako Pure Chemical Industries, Ltd.) for 6 days were treated with 0.5×TrypLE select, dissociated using a cell scraper, dispersed to single cells by pipetting, seeded in a 6-well culture plate coated with iMatrix-511 (Nippi) (0.5 μg/cm$^2$) at $2.0 \times 10^5$ cells per 1 well when AK03 medium or StemSure hPSC Medium Δ w/o bFGF was used and at $5.0 \times 10^5$ cells when Essential 8 medium was used, and cultured under 37° C., 5% $CO_2$ conditions. On the first day of culture, AK03 medium, Essential 8 medium or StemSure hPSC Medium Δ w/o bFGF added with Y-27632 (Wako Pure Chemical Industries, Ltd.) (final concentration 10 μM) as a ROCK inhibitor, SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration 10 μM), SB-431542 (final concentration 5 μM) and CKI-7 (final concentration 3 μM) was used; from 6 to 9 days of culture, the basal medium added with 15% KSR, Y-27632 (final concentration 10 μM), SB-431542 (final concentration 5 μM), CKI-7 (final concentration 3 μM) was used; from 10 to 13 days of culture, the basal medium added with 10% KSR, Y-27632 (final concentration 10 μM), SB-431542 (final concentration 5 μM), CKI-7 (final concentration 3 μM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 μg/ml streptomycin] was used. The whole amount of the medium was exchanged every day.

Figure 6:
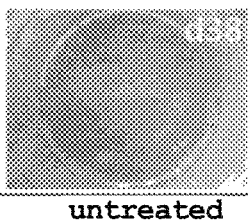
FIG. 6 shows photographs of 6-well culture plates after 38-42 days of culture containing iPS cell (201B7 or 1231A3)-derived differentiated cells produced by a production method without an FGF receptor inhibitor treatment step using "StemFit®" AK03 medium, Essential 8 medium or StemSure hPSC Medium Δ w/o bFGF.
Figure 6:
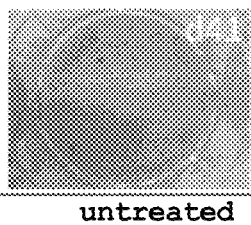
Figure 6:
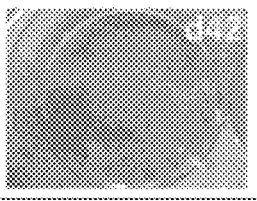
Figure 6:
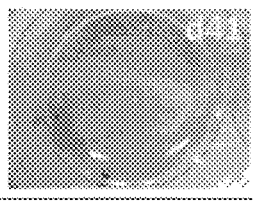
Figure 6:

The culture plate was observed from 38 to 42 days of culture. As a result, only a few cells could be confirmed to show typical characteristics of RPE cell such as a brown-black, polygonal, cobblestone-like morphology (FIG. 6).

Example 3: Highly Efficient Production of Retinal Pigment Epithelial Cells Including Combined Treatment Step of MEK Inhibitor and/or FGF Receptor Inhibitor and Various Inhibitors, Signal Transduction Pathway Inhibitor or Signal Transduction Pathway Agonist and Using Human iPS Cell Culture for maintaining undifferentiated state of human iPS cells (201B7 line and 1231A3 line) under feeder-free conditions was performed according to the method described in "Nakagawa, M. et. al., Sci. Rep. 2014 Jan. 8; 4: 3594". The medium used was "StemFit®" AK03 medium (Ajinomoto Co., Inc.) (hereinafter AK03 medium).

Production of retinal pigment epithelial (RPE) cells including a combined treatment step of MEK inhibitor and/or FGF receptor inhibitor, and various inhibitors, signal transduction pathway inhibitor or signal transduction pathway agonist was performed as follows. iPS cells under culture for maintaining undifferentiated state were treated with 0.5×TrypLE select, dissociated using a cell scraper, dispersed to single cells by pipetting, seeded in a 6-well culture plate coated with iMatrix-511 (Nippi) (0.5 μg/cm$^2$) at $1.2 \times 10^4$ cells per 1 well and cultured in a ROCK inhibitor [10 μM Y-27632 (Wako Pure Chemical Industries, Ltd.)]-containing AK03 medium under 37° C., 5% $CO_2$ conditions. The next day of cell seeding, PD0325901 (SIGMA) (final concentration 1 μM) as an MEK inhibitor, PD173074 (SIGMA) (final concentration 100 nM) as an FGF receptor inhibitor, LDN193189 (STEMGENT) (final concentration nM) as a BMP receptor inhibitor, SAG (Enzo Life Sciences) (final concentration 30 nM) as an Shh signal transduction pathway agonist, and Go6983 (SIGMA) (final concentration 2 μM) as a PKC inhibitor in the combination shown in FIG. 7 were added to the medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 μg/cm$^2$) at $2.0 \times 10^5$ cells per 1 well and cultured under 37° C., 5% $CO_2$ conditions (start of the second step). On the first day of culture, AK03 medium added with Y-(Wako Pure Chemical Industries, Ltd.) (final concentration 10 μM) as a ROCK inhibitor, SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration 10 μM), SB-431542 (final concentration 5 μM) and CKI-7 (final concentration 3 μM) was used; from 6 to 9 days of culture, the basal medium added with 15% KSR, Y-27632 (final concentration 10 μM), SB-431542 (final concentration 5 μM), CKI-7 (final concentration 3 μM) was used; from 10 to 13 days of culture, the basal medium added with 10% KSR, Y-27632 (final concentration 10 μM), SB-431542 (final concentration 5 μM), CKI-7 (final concentration 3 μM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 μg/ml streptomycin] was used. The whole amount of the medium was exchanged every day. Simultaneously, the experiment was also performed under the conditions of Example 1 containing an MEK inhibitor treatment step, Comparative Example 1 not containing an MEK inhibitor treatment step, Example 2 containing an FGF receptor inhibitor treatment step, and Comparative Example 2 not containing an FGF receptor inhibitor treatment step.

Figure 7:
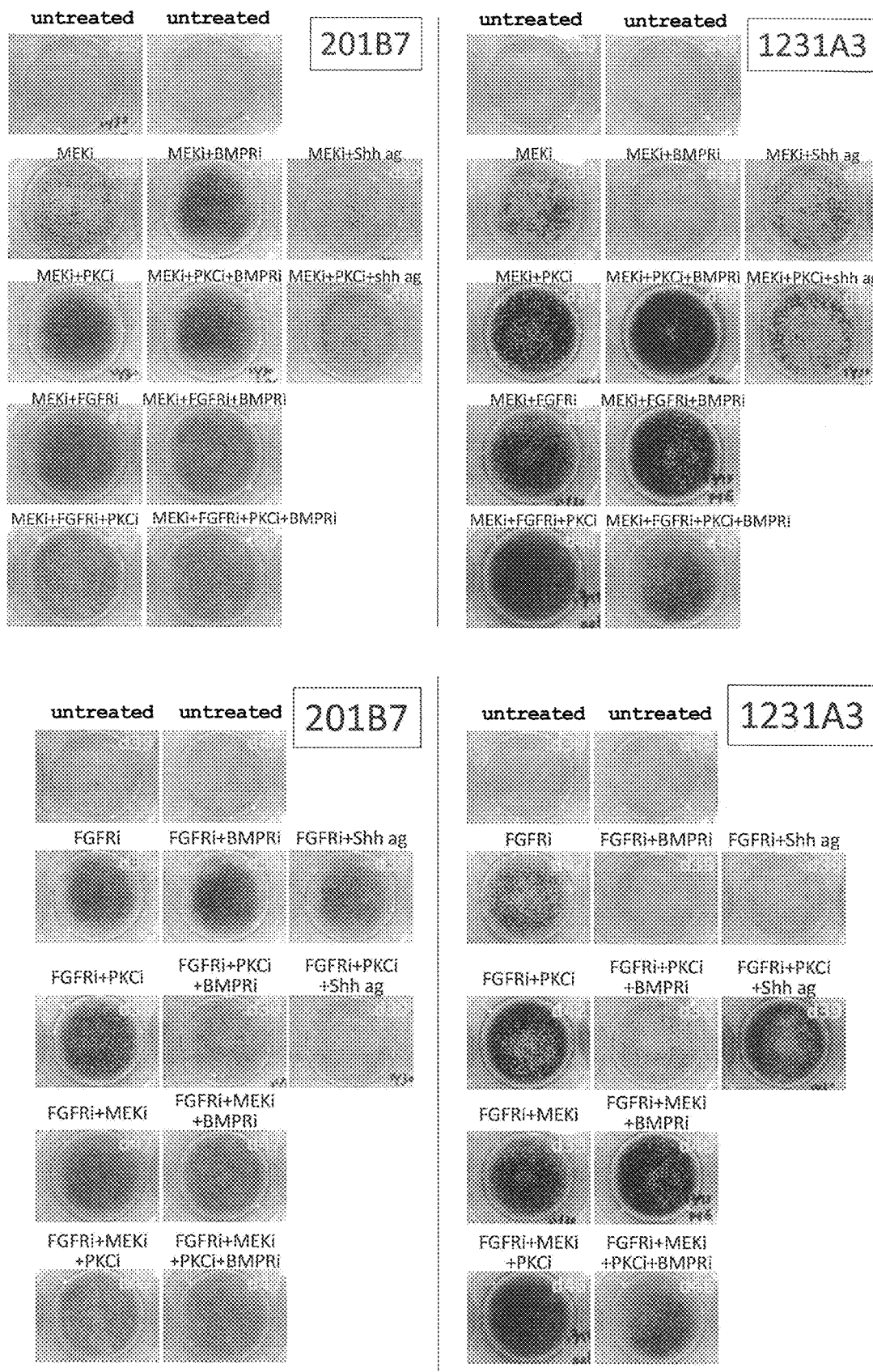
FIG. 7 shows photographs of 6-well culture plates after 38-47 days of culture containing iPS cell (201B7 or 1231A3)-derived RPE cells produced by a production method comprising a step for treating with combination of an MEK inhibitor and/or an FGF receptor inhibitor with various inhibitors, signal transduction pathway inhibitors or signal transduction pathway agonists. For comparison, photographs of 6-well culture plates containing iPS cell-derived RPE cells produced by a production method without an MEK inhibitor treatment step and a production method comprising an MEK inhibitor treatment step ("untreated" and "MEKi" in the upper panel of the figure), and photographs of 6-well culture plates containing iPS cell-derived RPE cells produced by a production method without an FGF receptor inhibitor treatment step and a production method comprising an FGF receptor inhibitor treatment step ("untreated" and "FGFRi" in the lower panel of the figure) are also shown. MEKi: MEK inhibitor (1 µM PD0325901), FGFRi: FGF receptor inhibitor (100 nM PD173074), BMPRi: BMP receptor inhibitor (100 nM LDN193189), Shh ag: Shh signal transduction pathway agonist (30 nM SAG), PKCi: PKC inhibitor (2 μM Go6983).
Figure 8:
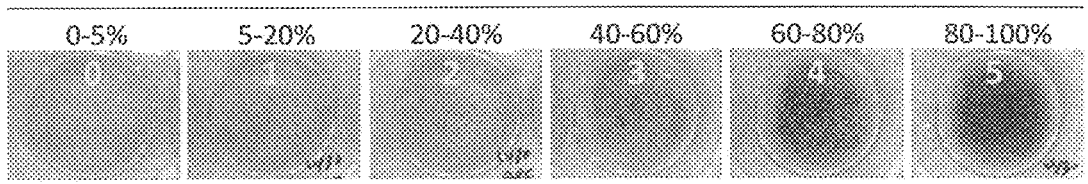
FIG. 8 shows (A) a representative photograph of 6-well culture plate of each scale when results are classified into a 6-point scale of 0 to 5 according to percentage of RPE cells in a whole well, (B) a summary of the results of productions by a production method without an MEK inhibitor treatment step (untreated), a production method comprising an MEK inhibitor treatment step (MEKi), and production methods comprising a step for treating with combination of an MEK inhibitor and various inhibitors or signal transduction pathway inhibitors (MEKi+PKCi, MEKi+PKCi+BMPRi, MEKi+FGFRi, MEKi+FGFRi+BMPRi, MEKi+FGFRi+PKCi, MEKi+FGFRi+PKCi+BMPRi), and (C) a summary of the results of productions by a production method without an FGF receptor inhibitor treatment step (untreated), a production method comprising an FGF receptor inhibitor treatment step (FGFRi), and production methods comprising a step for treating with combination of an FGF receptor inhibitor and various inhibitors or signal transduction pathway inhibitors (FGFRi+PKCi, FGFRi+PKCi+BMPRi, FGFRi+MEKi, FGFRi+MEKi+BMPRi, FGFRi+MEKi+PKCi, FGFRi+MEKi+PKCi+BMPRi). The vertical axes of the graphs show percentage of RPE cells in a whole well on a 6-point scale. The values are shown as mean±standard deviation, n shows the number of experiments. MEKi: MEK inhibitor (1 μM PD0325901), FGFRi: FGF receptor inhibitor (100 nM PD173074), BMPRi: BMP receptor inhibitor (100 nM LDN193189), PKCi: PKC inhibitor (2 μM Go6983).
Figure 8:
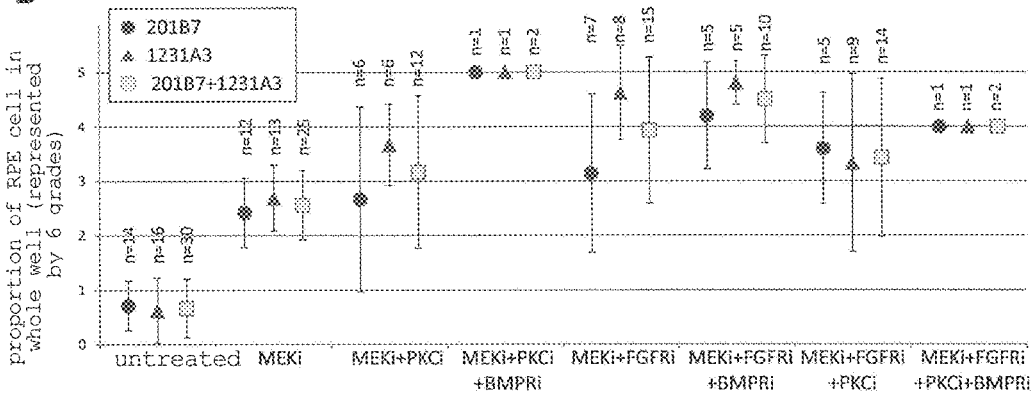
Figure 8:
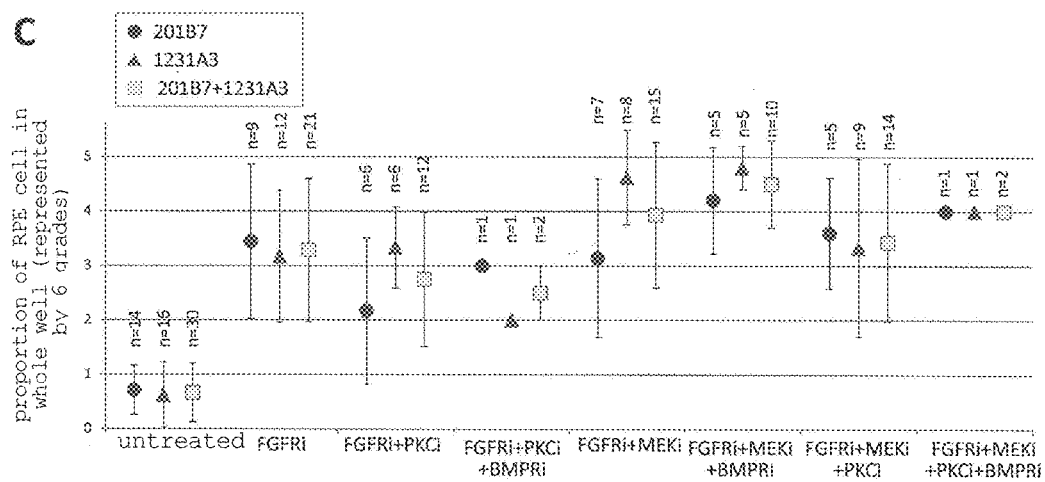

The culture plate was observed from 38 to 47 days of culture. As a result, only a few cells were found to show typical characteristics of RPE cell such as a brown-black, polygonal, cobblestone-like morphology under the conditions of Comparative Example 1 and Comparative Example 2 (FIG. 7, untreated). In contrast, under production conditions of Example 1 containing an MEK inhibitor treatment step, production conditions of Example 2 containing an FGF receptor inhibitor treatment step, and production conditions containing a combined treatment step of an MEK inhibitor and/or an FGF receptor inhibitor, and various inhibitors, a signal transduction pathway inhibitor or a signal transduction pathway agonist, emergence of RPE cells showing typical characteristics of RPE cell such as a brown-black, polygonal, cobblestone-like morphology could be confirmed (FIG. 7). The proportion of the RPE cells in the whole well was judged by visual observation and classification into 6 grades of 0 to 5 was performed according to the proportion (FIG. 8A). Under all compound combination treatment conditions shown in FIGS. 8B and 8C, emergence of RPE cells at a higher ratio than that under untreated condition could be confirmed (FIGS. 8B and 8C).

Example 4: Highly Efficient Production of Retinal Pigment Epithelial Cells Including MEK Inhibitor or FGF Receptor Inhibitor Treatment Step and Using Human iPS Cells Ff-I01, QHJI01

Culture for maintaining undifferentiated state of human iPS cells (Ff-I01 line and QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(−)), dissociated using a cell scraper, dispersed to single cells by pipetting, seeded in a 6-well culture plate coated with iMatrix-511 (Nippi) (0.5 μg/cm$^2$) at $2.0 \times 10^4$ cells per 1 well and cultured in a ROCK inhibitor [10 μM Y-27632 (Wako Pure Chemical Industries, Ltd.)]-containing AK03N medium under 37° C., 5% $CO_2$ conditions. On the next day of seeding, PD0325901 (SIGMA) (final concentration 1 μM) as an MEK inhibitor or PD173074 (SIGMA) (final concentration 100 nM) as an FGF receptor inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 μg/cm$^2$) at $2.0 \times 10^5$ cells per 1 well and cultured under 37° C., 5% $CO_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-(final concentration 10 μM), SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 5 to 8 days of culture, the basal medium added with 15% KSR, Y-27632 (final concentration 10 μM), SB-431542 (final concentration 5 μM), CKI-7 (final concentration 3 μM) was used; from 9 to 12 days of culture, the basal medium added with 10% KSR, Y-27632 (final concentration μM), SB-431542 (final concentration 5 μM), CKI-7 (final concentration 3 μM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 μg/ml streptomycin] was used. The whole amount of the medium was exchanged every day. Simultaneously, the experiment was also performed under the conditions of Comparative Example 1 not containing an MEK inhibitor treatment step (provided that AK03 medium was changed to AK03N medium) and Comparative Example 2 not containing an FGF receptor inhibitor treatment step (provided that AK03 medium was changed to AK03N medium).

Figure 9:
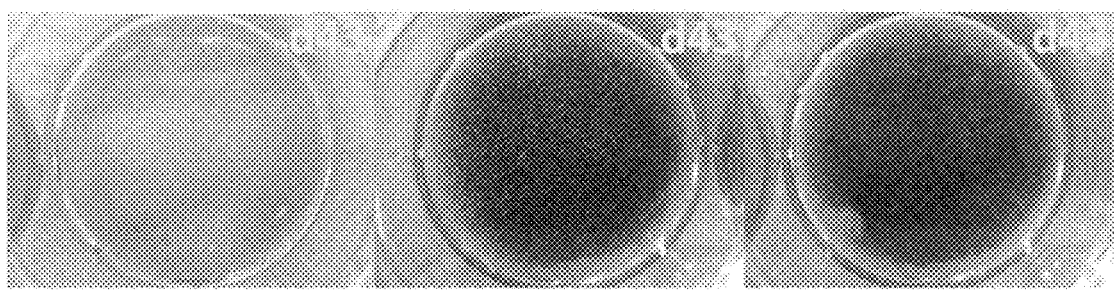
FIG. 9 shows photographs of 6-well culture plates after 43 days of culture containing iPS cell (Ff-I01 or QHJI01)-derived retinal pigment epithelial (RPE) cells produced by a production method comprising an MEK inhibitor or FGF receptor inhibitor treatment step using "StemFit®" AK03N medium (MEKi or FGFRi). For comparison, photographs of 6-well culture plates after 43 days of culture containing iPS cell-derived differentiated cells produced by production methods without an MEK inhibitor and/or FGF receptor inhibitor treatment step are also shown (untreated). MEKi: MEK inhibitor (1 μM PD0325901), FGFRi: FGF receptor inhibitor (100 nM PD173074).
Figure 9:
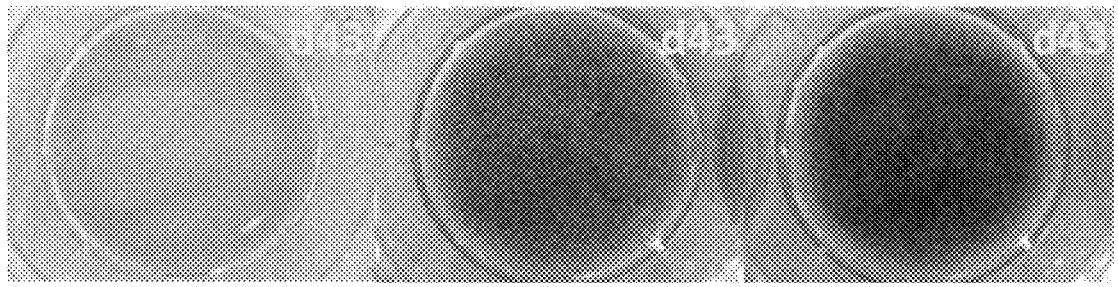

The culture plate was observed on day 43 of culture. As a result, there was found almost no cell that showed typical characteristics of RPE cell such as a brown-black, polygonal, cobblestone-like morphology under the conditions of Comparative Example 1 and Comparative Example 2 (FIG. 9, untreated). On the other hand, when exposed to the MEK inhibitor and FGF receptor inhibitor, emergence of a brown-black cell population could be confirmed over a wide area in the both lines of Ff-I01 line and QHJI01 line (FIG. 9, MEKi, FGFRi).

Example 5: Consideration of Number of Days of Exposure of Each Inhibitor in MEK Inhibitor or FGF Receptor Inhibitor Treatment Step Culture for maintaining undifferentiated state of human iPS cells (QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(−)), dissociated using a cell scraper, dispersed to single cells by pipetting, seeded in a 6-well culture plate coated with iMatrix-511 (Nippi) (0.5 μg/cm$^2$) at $2.0 \times 10^4$ cells per 1 well and cultured in a ROCK inhibitor [10 μM Y-27632 (Wako Pure Chemical Industries, Ltd.)]-containing AK03N medium under 37° C., 5% $CO_2$ conditions. On the next day of seeding, 2 days later, 3 days later, 4 days later, 5 days later or 6 days later, PD0325901 (SIGMA) (final concentration 1 μM) as an MEK inhibitor or PD173074 (SIGMA) (final concentration 100 nM) as an FGF receptor inhibitor was added to the AK03N medium (start of the first step) and the cells were exposed thereto for 6 days, 5 days, 4 days, 3 days, 2 days or 1 day (completion of the first step). Thereafter, the cells were treated with 0.5×TrypLE select, dissociated using a cell scraper, dispersed to single cells by pipetting, seeded in a 6-well culture plate coated with iMatrix-511 (0.5 μg/cm$^2$) at $2.0 \times 10^3$ cells per 1 well and cultured under 37° C., 5% $CO_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration μM), SB-431542 (Wako Pure Chemical Industries, Ltd.) (final concentration 5 μM) as Nodal signal transduction pathway inhibitor, and CKI-7 (SIGMA) (final concentration 3 μM) as Wnt signal transduction pathway inhibitor was used; from 5 to 8 days of culture, the basal medium added with 15% KSR, Y-27632 (final concentration 10 μM), SB-431542 (final concentration 5 μM), CKI-7 (final concentration 3 μM) was used; from 9 to 12 days of culture, the basal medium added with 10% KSR, Y-27632 (final concentration 10 µM), SB-431542 (final concentration 5 µM), CKI-7 (final concentration 3 µM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day.

Figure 10:
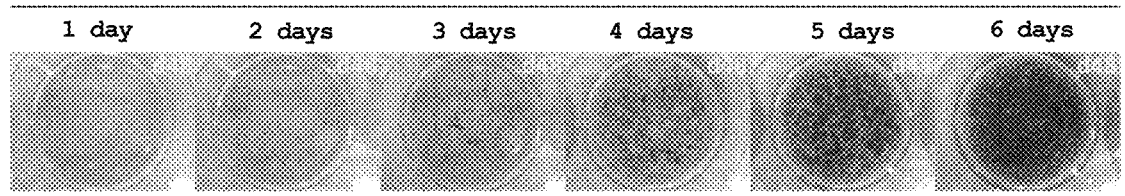
FIG. 10 shows photographs of 6-well culture plates after 48 days of culture containing iPS cell (QHJI01)-derived retinal pigment epithelial (RPE) cells produced by a production method comprising an MEK inhibitor or FGF receptor inhibitor treatment step using "StemFit®" AK03N medium (MEKi (PD0325901) or FGFRi(PD173074)). Effects of exposure to the inhibitors for 1 day to 6 days were examined. MEKi: MEK inhibitor (1 μM PD0325901), FGFRi: FGF receptor inhibitor (100 nM PD173074).
Figure 10:
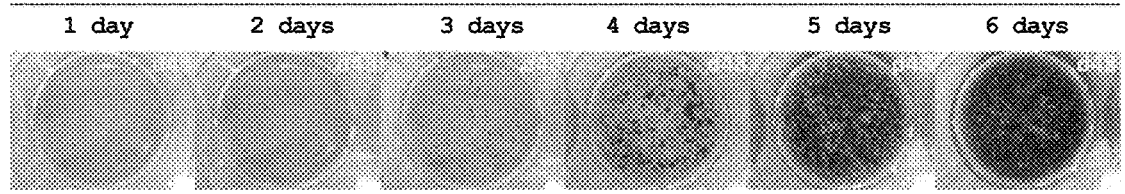

The culture plate was observed on day 48 of culture. As a result, in the both treatments with the MEK inhibitor and FGF receptor inhibitor, brown-black cell populations increased by exposure for not less than 2 days, and the proportion of cells that developed color in the whole well increased as the number of exposure day increased up to 6 days of exposure (FIG. 10). Particularly, a remarkable increase in the brown-black cell population was seen in 4 days-6 days of exposure.

Example 6: Consideration of MEK Inhibitor Exposure Period in MEK Inhibitor Treatment Step Culture for maintaining undifferentiated state of human iPS cells (1231A3 line) under feeder-free conditions was performed according to the method described in "Nakagawa, M. et. al., Sci. Rep. 2014 Jan. 8; 4: 3594". The medium used was "StemFit®" AK03 medium (Ajinomoto Co., Inc.) (hereinafter AK03 medium).

Production of retinal pigment epithelial (RPE) cells including an MEK inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(−)), dissociated using a cell scraper, dispersed to single cells by pipetting, seeded in a 6-well culture plate coated with iMatrix-511 (Nippi) (0.5 µg/cm$^2$) at 1.2×10$^4$ cells per 1 well and cultured in a ROCK inhibitor [10 µM Y-27632 (Wako Pure Chemical Industries, Ltd.)]-containing AK03 medium under 37° C., 5% $CO_2$ conditions. On the next day of seeding, 4 days later or 6 days later, PD0325901 (SIGMA) (final concentration 1 µM) as an MEK inhibitor was added to the AK03 medium (start of the first step) and the cells were exposed thereto for 6 days, 3 days or 1 day (completion of the first step). In addition, cells exposed to MEK inhibitor for 6 days were treated with 0.5×TrypLE select, dissociated using a cell scraper, dispersed to single cells by pipetting, seeded in a 6-well culture plate coated with iMatrix-511 (Nippi) (0.5 µg/cm$^2$) at 0.8×10$^4$ cells per 1 well and further cultured for 7 days in AK03 medium containing Y-27632 (final concentration 10 µM) and PD0325901 (final concentration 1 µM) under 37° C., 5% $CO_2$ conditions, whereby the cells were exposed to the MEK inhibitor for 13 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 µg/cm$^2$) at 1.2×10$^6$ cells per 1 well and cultured under 37° C., 5% $CO_2$ conditions (start of the second step). On day 1 of culture, AK03 medium added with Y-27632 (final concentration 10 µM), SB-(Wako Pure Chemical Industries, Ltd.) (final concentration 5 µM) as Nodal signal transduction pathway inhibitor, and CKI-7 (SIGMA) (final concentration 3 µM) as Wnt signal transduction pathway inhibitor was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration µM), SB-431542 (final concentration 5 µM) and CKI-7(final concentration 3 µM) was used; from 6 to 9 days of culture, the basal medium added with 15% KSR, Y-27632 (final concentration µM), SB-431542 (final concentration 5 µM), CKI-7 (final concentration 3 µM) was used; from 10 to 13 days of culture, the basal medium added with 10% KSR, Y-27632 (final concentration 10 µM), SB-431542 (final concentration 5 µM), CKI-7 (final concentration 3 µM) was used; from 14 to 30 days of culture, a basal medium added with 10% KSR alone was used; and from 31 days and thereafter of culture, RPE maintenance medium [67% DMEM low glucose (SIGMA), 29% F12 (SIGMA), 1.9% B-supplement (Life Technologies), 1.9 mM L-glutamine, 96 U/ml penicillin-96 µg/ml streptomycin] was used. The whole amount of the medium was exchanged every day. Simultaneously, RPE cells were also produced under the conditions of Comparative Example 1 not containing an MEK inhibitor treatment step.

Figure 11:
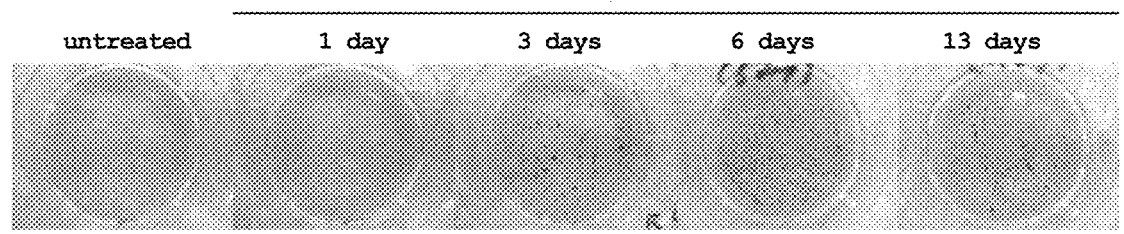
FIG. 11 shows photographs of 6-well culture plates after 37 days of culture containing iPS cell (1231A3)-derived retinal pigment epithelial (RPE) cells produced by a production method comprising an MEK inhibitor treatment step using "StemFit®" AK03N medium (MEKi (PD0325901)). For comparison, a photograph of 6-well culture plate after 37 days of culture containing iPS cell-derived differentiated cells produced by a production method without an MEK inhibitor treatment step is also shown (untreated). Effects of exposure to the inhibitor for 1 day, 3 days, 6 days and 13 days were examined. MEKi: MEK inhibitor (1 μM PD0325901).

The culture plate was observed on day 37 of culture. As a result, there was found almost no cell that showed typical characteristics of RPE cell such as a brown-black, polygonal, cobblestone-like morphology under the conditions of Comparative Example 1 and exposure to MEK inhibitor for one day (FIG. 11, untreated, MEKi 1 day). On the other hand, emergence of a brown-black cell population could be confirmed over a wide area by exposure to the MEK inhibitor for 3 days and 6 days (FIG. 11, MEKi 3 days, 6 days), and sufficient emergence of colored cell population was also confirmed similarly by exposure for 13 days (FIG. 11, MEKi 13 days).

Example 7: Gene Expression on Completion of MEK Inhibitor or FGF Receptor Inhibitor Treatment Step Culture for maintaining undifferentiated state of human iPS cells (Ff-I01 line and QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(−)), dissociated using a cell scraper, dispersed to single cells by pipetting, seeded in a 6-well culture plate coated with iMatrix-511 (Nippi) (0.5 µg/cm$^2$) at 2.0×10$^4$ cells per 1 well and cultured in a ROCK inhibitor [10 µM Y-27632 (Wako Pure Chemical Industries, Ltd.)]-containing AK03N medium under 37° C., 5% $CO_2$ conditions. On the next day of seeding or 4 days later, PD0325901 (SIGMA) (final concentration 1 µM) as an MEK inhibitor or PD173074 (SIGMA) (final concentration 100 nM) as an FGF receptor inhibitor was added to the AK03N medium (start of the first step) and the cells were exposed thereto for 6 days or 3 days (completion of the first step). Thereafter, the cells were treated with 0.5×TrypLE select, dissociated using a cell scraper, dispersed to single cells by pipetting, the cells other than those to be transferred to the second step were used for RNA extraction as a sample for microarray, the cells to be transferred to the second step were seeded in a 6-well culture plate coated with iMatrix-511 (0.5 μg/cm$^2$) at 2.0×10$^5$ cells per 1 well and cultured under 37° C., 5% CO$_2$ conditions (start of the second step). On day 1 of culture, AK03 medium added with Y-27632 (final concentration 10 μM), SB-431542 (Wako Pure Chemical Industries, Ltd.) (final concentration 5 μM) as Nodal signal transduction pathway inhibitor, and CKI-7(SIGMA)(final concentration 3 μM) as Wnt signal transduction pathway inhibitor, or a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration μM), SB-431542 (Wako Pure Chemical Industries, Ltd.) (final concentration 5 μM) and CKI-7 (SIGMA) (final concentration 3 μM) was used. When the AK03 medium (containing Y-27632, SB- and CKI-7) was used on day 1 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration 10 μM), SB-431542 (Wako Pure Chemical Industries, Ltd.) (final concentration 5 μM) and CKI-7 (SIGMA) (final concentration 3 μM) was used from to 5 days of culture; from 6 to 9 days of culture, the basal medium added with 15% KSR, Y-27632 (final concentration 10 μM), SB-431542 (final concentration 5 μM), CKI-7 (final concentration 3 μM) was used; from 10 to 13 days of culture, the basal medium added with 10% KSR, Y-27632 (final concentration 10 μM), SB-431542 (final concentration 5 μM), CKI-7 (final concentration 3 μM) was used; from 14 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-supplement (Life Technologies), 1.9 mM L-glutamine, 96 U/ml penicillin-96 μg/ml streptomycin] was used. When a basal medium (containing 20% KSR, Y-27632, SB-431542 and CKI-7) was used on day 1 of culture, from 2 to 4 days of culture, a basal medium added with 20% KSR (Life Technologies), Y-27632 (final concentration 10 μM), SB-431542 (final concentration 5 μM) and CKI-7 (final concentration 3 μM) was used; from 5 to 8 days of culture, a basal medium added with 15% KSR, Y-27632 (final concentration 10 μM), SB-431542 (final concentration 5 μM) and CKI-7 (final concentration 3 μM) was used; from 9 to 12 days of culture, a basal medium added with 10% KSR, Y-27632 (final concentration 10 μM), SB-431542 (final concentration 5 μM) and CKI-7 (final concentration 3 μM) was used; from 13 to 30 days of culture, a basal medium added with 10% KSR alone was used; and from 31 days and thereafter of culture, RPE maintenance medium was used. The whole amount of the medium was exchanged every day. Simultaneously, recovery of sample for microarray and production of RPE cell were also performed under the conditions of Comparative Example 1 not containing an MEK inhibitor treatment step (AK03 medium was changed to AK03N medium).

RNeasy Mini Kit (QIAGEN) was used for extraction of RNA, and microarray analysis was performed using GeneChip Human Genome U133 Plus 2.0 Array (Affymetrix). For microarray analysis, entrusted analysis by KURABO INDUSTRIES LTD. was utilized.

Based on the observed images of culture plates on day 43 of culture and according to FIG. 8A, the results of the determined proportion of RPE cells in the whole well by visual observation (scored in 6 grades of 0 to 5 according to the proportion of RPE cells) and expression values (Signal) and flag (Detection) of markers in the early stage of eye formation PAX6, LHX2, SIX3 on completion of the first step, which are the microarray analysis results, are summarized in Table (FIG. 12). The flag expresses the reliability of the expression value, P means high reliability and A means low reliability. From these results, a correlation was found between the proportion of RPE cells in the whole well and the expression values of PAX6, LHX2, and SIX3 on completion of the first step. Therefore, it was found that the transition time to the second step can be determined based on the expression of these genes.

Example 8: Consideration of Various Inhibitor Concentrations in MEK Inhibitor or FGF Receptor Inhibitor Treatment Step Culture for maintaining undifferentiated state of human iPS cells (QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(-)), dissociated using a cell scraper, dispersed to single cells by pipetting, seeded in a 6-well culture plate coated with iMatrix-511 (Nippi) (0.5 μg/cm$^2$) at 2.0×10$^4$ cells per 1 well and cultured in a ROCK inhibitor [10 μM Y-27632 (Wako Pure Chemical Industries, Ltd.)]-containing AK03N medium under 37° C., 5% CO$_2$ conditions. On the next day of seeding, PD0325901 (SIGMA) at a final concentration of 0.25 μM, 0.5 μM, 1 μM, 2 μM or 4 μM as MEK inhibitor and PD173074 (SIGMA) at a final concentration of 25 nM, 50 nM, 100 nM, 200 nM or 400 nM as FGF receptor inhibitor were added to the AK03N medium (start of the first step) and the cells were exposed thereto for 6 days (completion of the first step). Thereafter, the cells were treated with 0.5× TrypLE select, dissociated using a cell scraper, dispersed to single cells by pipetting, seeded in a 6-well culture plate coated with iMatrix-511 (0.5 μg/cm$^2$) at 2.0×10$^5$ cells per 1 well and cultured under 37° C., 5% CO$_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-(final concentration 10 μM), SB-431542 (Wako Pure Chemical Industries, Ltd.) (final concentration 5 μM) as Nodal signal transduction pathway inhibitor and CKI-7 (SIGMA) (final concentration 3 μM) as Wnt signal transduction pathway inhibitor was used; from 5 to 8 days of culture, the basal medium added with 15% KSR, Y-27632 (final concentration 10 μM), SB-431542 (final concentration 5 μM), CKI-7 (final concentration 3 μM) was used; from 9 to 12 days of culture, the basal medium added with 10% KSR, Y-27632 (final concentration μM), SB-431542 (final concentration 5 µM), CKI-7 (final concentration 3 µM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day. Simultaneously, production of RPE cell were also performed under the conditions of Comparative Example 1 not containing an MEK inhibitor treatment step (AK03 medium was changed to AK03N medium) and the conditions of Comparative Example 2 not containing an FGF receptor inhibitor treatment step (AK03 medium was changed to AK03N medium).

Figure 13:
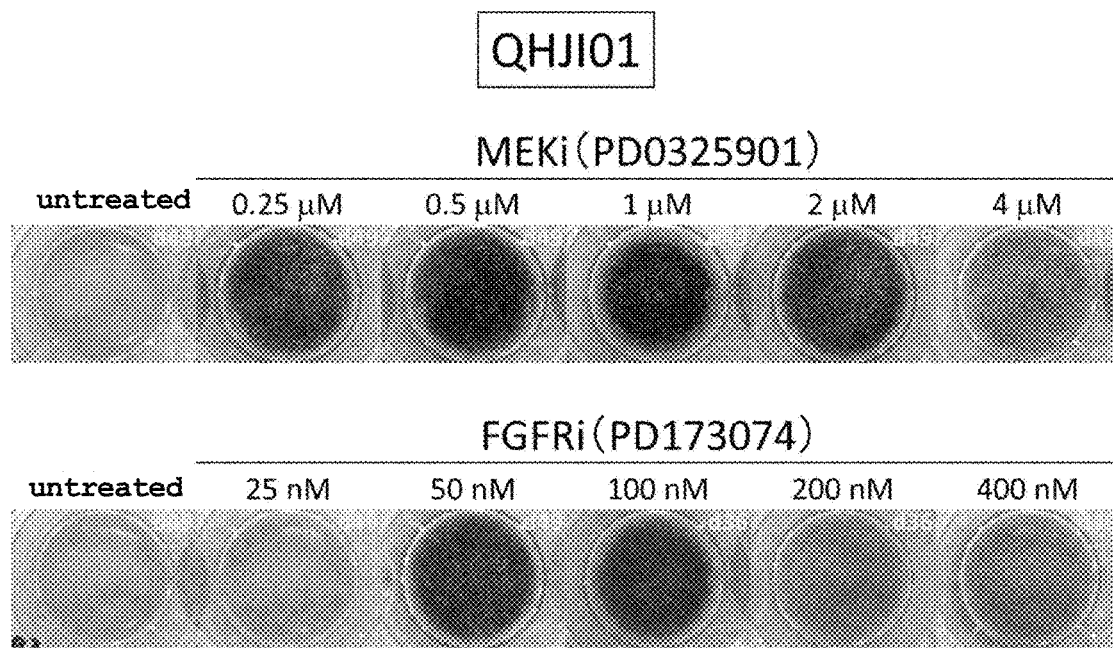
FIG. 13 shows photographs of 6-well culture plates after 36 days or 49 days of culture containing iPS cell (QHJI01)-derived retinal pigment epithelial (RPE) cells produced by a production method comprising an MEK inhibitor or FGF receptor inhibitor treatment step using "StemFit®" AK03N medium (MEKi (PD0325901) or FGFRi(PD173074)). For comparison, photographs of 6-well culture plates after 49 days of culture containing iPS cell-derived differentiated cells produced by a production method without an MEK inhibitor and/or FGF receptor inhibitor treatment step are also shown (untreated). Effects of MEK inhibitor in concentrations of 0.25 μM-4 μM, or FGF receptor inhibitor in concentrations of 25 nM-400 nM were examined. MEKi: MEK inhibitor (PD0325901), FGFRi: FGF receptor inhibitor (PD173074).

The culture plate was observed on day 36 and day 49 of culture. As a result, there was found almost no cell that showed typical characteristics of RPE cell such as a brown-black, polygonal, cobblestone-like morphology under the conditions of Comparative Example 1 and Comparative Example 2 (FIG. 13, untreated). On the other hand, emergence of a brown-black cell population could be confirmed over a wide area at all MEK inhibitor concentrations (0.25-4 µM) and FGF receptor inhibitor concentrations (25-400 nM) studied (FIG. 13, MEKi: 0.25-4 µM, FGFRi: 25-400 nM).

Example 9: Consideration of Seeded Cell Number in Transition of First Step to Second Step Culture for maintaining undifferentiated state of human iPS cells (QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(-)), dissociated using a cell scraper, dispersed to single cells by pipetting, seeded in a 6-well culture plate coated with iMatrix-511 (Nippi) (0.5 µg/cm$^2$) at 2.0×10$^4$ cells per 1 well and cultured in a ROCK inhibitor [10 µM Y-27632 (Wako Pure Chemical Industries, Ltd.)]-containing AK03N medium under 37° C., 5% CO$_2$ conditions. On the next day of seeding, PD0325901 (SIGMA) (final concentration 1 µM) as MEK inhibitor or PD173074 (SIGMA) (final concentration nM) as FGF receptor inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting seeded in a 6-well culture plate coated with iMatrix-511 (0.5 µg/cm$^2$) at 0.2, 0.4, 0.6, 1.0, 2.0 or 4.0×10$^5$ cells (0.2, 0.4, 0.6, 1.0, 2.0 or 4.0×10$^4$ cells/cm$^2$) per 1 well and cultured under 37° C., 5% CO$_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration µM), SB-431542 (Wako Pure Chemical Industries, Ltd.) (final concentration 5 µM) as Nodal signal transduction pathway inhibitor and CKI-7 (SIGMA) (final concentration 3 µM) as Wnt signal transduction pathway inhibitor was used; from 5 to 8 days of culture, the basal medium added with 15% KSR, Y-27632 (final concentration 10 µM), SB-431542 (final concentration 5 µM), CKI-7 (final concentration 3 µM) was used; from 9 to 12 days of culture, the basal medium added with 10% KSR, Y-27632 (final concentration 10 µM), SB-431542 (final concentration 5 µM), CKI-7 (final concentration 3 µM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day.

Figure 14:
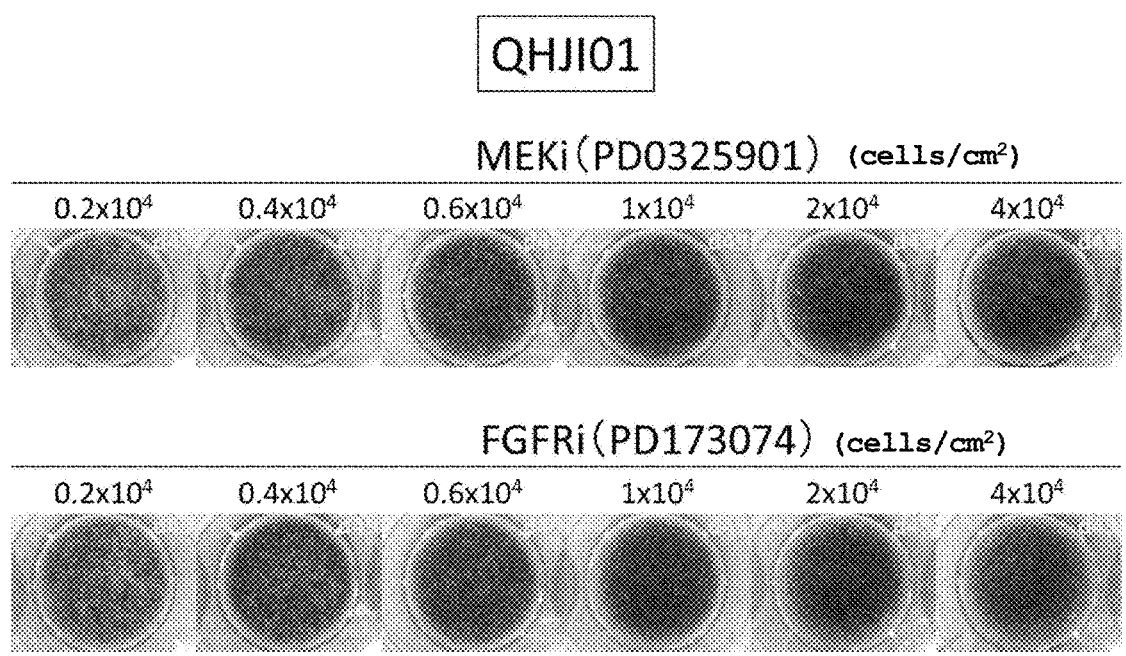
FIG. 14 shows photographs of 6-well culture plates after 49 days of culture containing iPS cell (QHJI01)-derived retinal pigment epithelial (RPE) cells produced by a production method comprising an MEK inhibitor or FGF receptor inhibitor treatment step using "StemFit®" AK03N medium (MEKi (PD0325901) or FGFRi(PD173074)). Effects of the number of cells plated at the beginning of the second step ($0.2 \times 10^4$-$4.0 \times 10^4$ cells/cm$^2$) were examined. MEKi: MEK inhibitor (1 μM PD0325901), FGFRi: FGF receptor inhibitor (100 nM PD173074).

The culture plate was observed on day 49 of culture. As a result, emergence of a brown-black cell population could be confirmed over a wide area at all seeded cell number (0.2, 0.4, 0.6, 1.0, 2.0, or, 4.0×10$^4$ cells/cm$^2$) studied (FIG. 14).

Example 10: Consideration of MEK Inhibitors PD184352, U0126, TAK-733, AZD-8330 in First Step Undifferentiated maintenance culture of human iPS cells (QHJI01 line and 1231A3 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor treatment step was performed as follows. iPS cells under culture for maintaining undifferentiated state were treated with 0.5× TrypLE select (mixture of equal amounts of TrypLE select (Life Technologies) and 0.5 mM EDTA/PBS(-)), dissociated using a cell scraper, dispersed to single cells by pipetting, seeded in a 6-well culture plate coated with iMatrix-511 (Nippi) (0.5 µg/cm$^2$) at 2.0×10$^4$ cells per 1 well and cultured in a ROCK inhibitor [10 µM Y-27632 (Wako Pure Chemical Industries, Ltd.)]-containing AKO3N medium under 37° C., 5% CO$_2$ conditions. On the next day of seeding, PD0325901 (SIGMA) (final concentration 1 µM), PD184352 (SIGMA) (final concentration 1.5 µM, 3 µM, 6 µM), U0126 (SIGMA) (final concentration 5 µM, 10 µM), TAK-733 (Selleck) (final concentration 0.3 µM) or AZD-8330 (Selleck) (final concentration 0.3 µM) as MEK inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 µg/cm$^2$) at 2.0×10$^5$ cells per 1 well and cultured under 37° C., 5% CO$_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration 10 µM), SB-431542 (Wako Pure Chemical Industries, Ltd.) (final concentration 5 µM) as Nodal signal transduction pathway inhibitor and CKI-7 (SIGMA) (final concentration 3 µM) as Wnt signal transduction pathway inhibitor was used; from 5 to 8 days of culture, the basal medium added with 15% KSR, Y-27632 (final concentration 10 µM), SB-431542 (final concentration 5 µM), CKI-7 (final concentration 3 µM) was used; from 9 to 12 days of culture, the basal medium added with 10% KSR, Y-27632 (final concentration 10 µM), SB-431542 (final concentration 5 µM), CKI-7 (final concentration 3 µM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day. Simultaneously, RPE cells were also produced under the conditions of Comparative Example 1 not containing an MEK inhibitor treatment step (AK03 medium was changed to AK03N medium).

Figure 15:
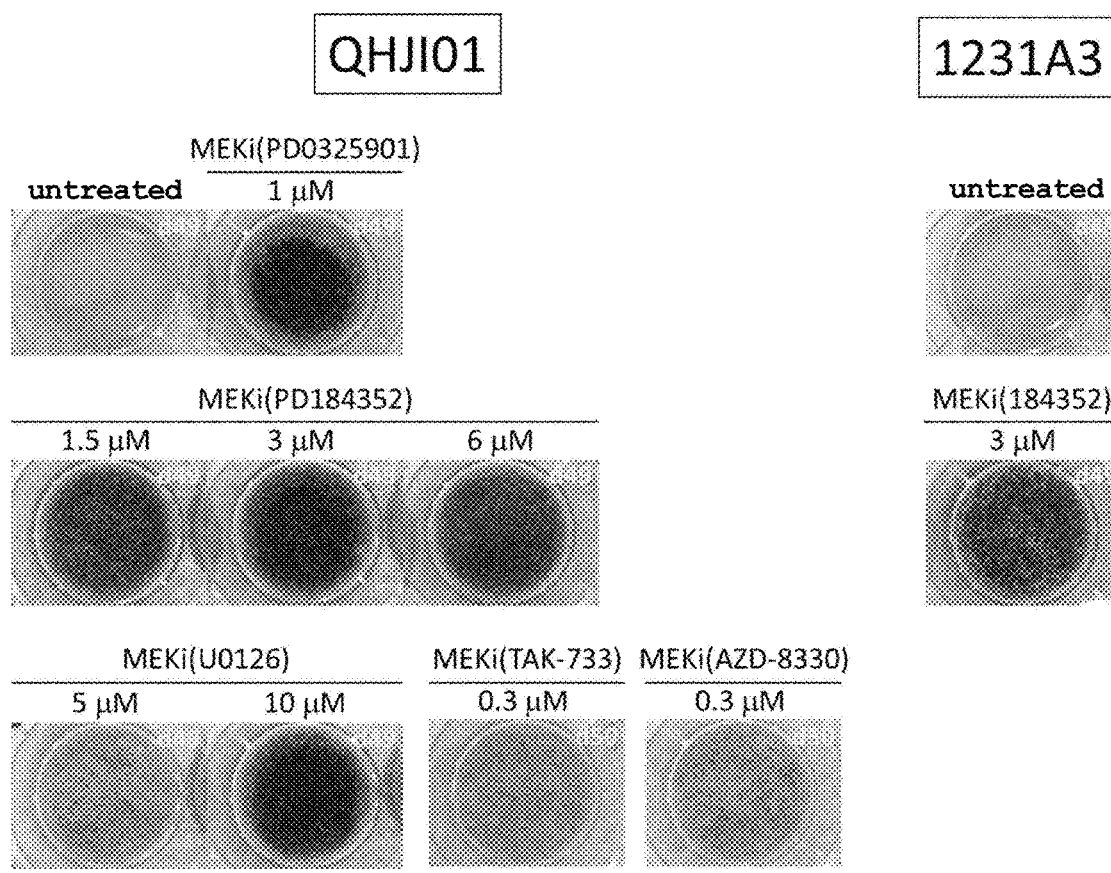
FIG. 15 shows photographs of 6-well culture plates after 49 days or 50 days of culture containing iPS cell (QHJI01 or 1231A3)-derived retinal pigment epithelial (RPE) cells produced by a production method comprising an MEK inhibitor treatment step using "StemFit®" AK03N medium (MEKi (PD0325901), MEKi (PD184352), MEKi (U0126), MEKi (TAK-733) or MEKi(AZD-8330)). For comparison, photographs of 6-well culture plates after 49 days of culture containing iPS cell-derived differentiated cells produced by a production method without an MEK inhibitor treatment step are also shown (untreated). MEKi: MEK inhibitor (1 μM PD0325901, 1.5 μM, 3 μM or 6 μM PD184352, 5 μM or 10 μM U0126, 0.3 μM TAK-733, 0.3 μM AZD-8330).

The culture plate was observed on day 49 and day 50 of culture. As a result, there was found almost no cell that showed typical characteristics of RPE cell such as a brown-black, polygonal, cobblestone-like morphology under the conditions of Comparative Example 1 (FIG. 15, untreated). On the other hand, emergence of a brown-black cell population could be confirmed over a wide area in all MEK inhibitors (PD0325901, PD184352, U0126, TAK-733, AZD-8330) studied (FIG. 15, PD0325901, PD184352, U0126, TAK-733, AZD-8330).

Example 11: Consideration of FGF Receptor Inhibitor SU5402 in First Step

Culture for maintaining undifferentiated state of human iPS cells (QHJI01 line and 1231A3 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(-)), dissociated using a cell scraper, dispersed to single cells by pipetting, seeded in a 6-well culture plate coated with iMatrix-511 (Nippi) (0.5 µg/cm$^2$) at 2.0×10$^4$ cells per 1 well and cultured in a ROCK inhibitor [10 µM Y-27632 (Wako Pure Chemical Industries, Ltd.)]-containing AK03N medium under 37° C., 5% CO$_2$ conditions. On the next day of seeding, PD173074 (SIGMA) (final concentration 100 nM) or SU5402 (SIGMA) (final concentration 5 µM, 10 µM, 20 µM) as FGF receptor inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 µg/cm$^2$) at 2.0×10$^5$ cells per 1 well and cultured under 37° C., 5% OO$_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration µM), SB-431542 (Wako Pure Chemical Industries, Ltd.) (final concentration 5 µM) as Nodal signal transduction pathway inhibitor and CKI-7 (SIGMA) (final concentration 3 µM) as Wnt signal transduction pathway inhibitor was used; from 5 to 8 days of culture, the basal medium added with 15% KSR, Y-27632 (final concentration 10 µM), SB-431542 (final concentration 5 µM), CKI-7 (final concentration 3 µM) was used; from 9 to 12 days of culture, the basal medium added with 10% KSR, Y-27632 (final concentration 10 µM), SB-431542 (final concentration 5 µM), CKI-7 (final concentration 3 µM) was used; from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day. Simultaneously, RPE cells were also produced under the conditions of Comparative Example 2 not containing an FGF receptor inhibitor treatment step (AK03 medium was changed to AK03N medium).

Figure 16:
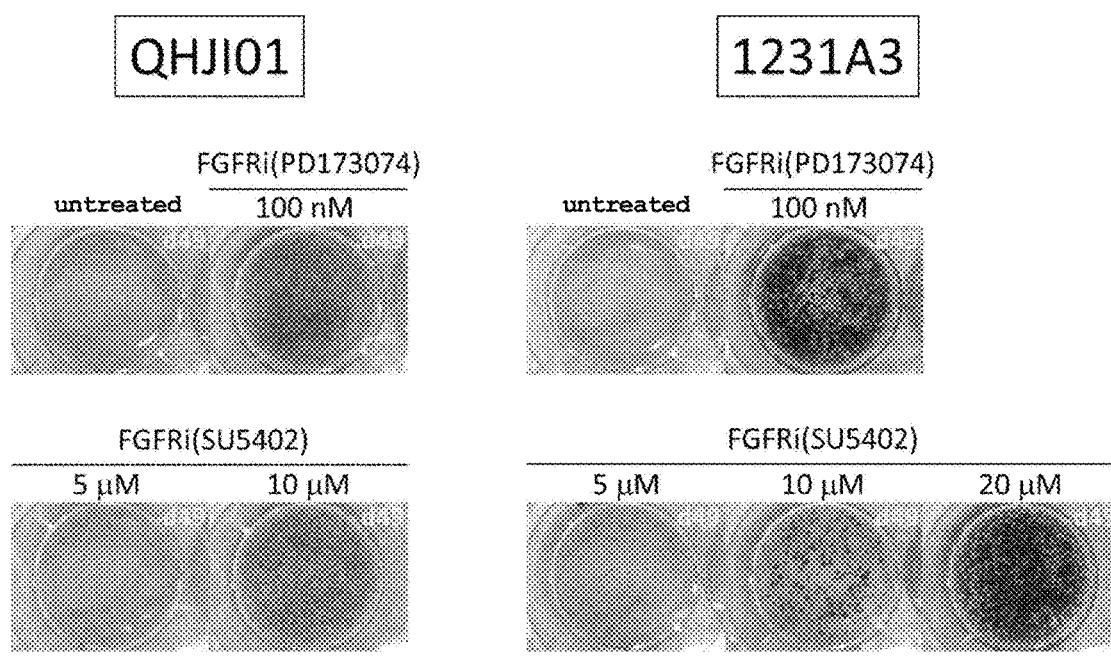
FIG. 16 shows photographs of 6-well culture plates after 49 days of culture containing iPS cell (QHJI01 or 1231A3)-derived retinal pigment epithelial (RPE) cells produced by a production method comprising an FGF receptor inhibitor treatment step using "StemFit®" AK03N medium (FGFRi (PD173074), or FGFRi (SU5402)). For comparison, photographs of 6-well culture plates after 49 days of culture containing iPS cell-derived differentiated cells produced by a production method without an FGF receptor inhibitor treatment step are also shown (untreated). FGFRi: FGF receptor inhibitor (100 nM PD173074, 5 μM, 10 μM or 20 μM SU5402).

The culture plate was observed on day 49 of culture. As a result, there was found almost no cell that showed typical characteristics of RPE cell such as a brown-black, polygonal, cobblestone-like morphology under the conditions of Comparative Example 2 (FIG. 16, untreated). On the other hand, emergence of a brown-black cell population could be confirmed over a wide area in all FGF receptor inhibitors (PD173074, SU5402) studied (FIG. 16, PD173074, SU5402).

Example 12: Consideration of Differentiation Induction Effect of Exposure of Nodal Signal Transduction Pathway Inhibitor and Wnt Signal Transduction Pathway Inhibitor Alone in Second Step Culture for maintaining undifferentiated state of human iPS cells (QHJI01 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(-)), dissociated using a cell scraper, dispersed to single cells by pipetting, seeded in a 6-well culture plate coated with iMatrix-511 (Nippi) (0.5 µg/cm$^2$) at 2.0×10$^4$ cells per 1 well and cultured in a ROCK inhibitor [10 µM Y-27632 (Wako Pure Chemical Industries, Ltd.)]-containing AK03N medium under 37° C., 5% CO$_2$ conditions. On the next day of seeding, PD0325901 (SIGMA) (final concentration 1 µM) as MEK inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 12-well culture plate coated with iMatrix-511 (0.5 µg/cm$^2$) at 0.8×10$^5$ cells per 1 well and cultured under 37° C., 5% CO$_2$ conditions (start of the second step). In the second step, the following kinds of media were used. From day 1 to day 12 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 10% KSR (Life Technologies), Y-27632 (final concentration µM), SB-431542 (Wako Pure Chemical Industries, Ltd.) (final concentration 5 µM) as Nodal signal transduction pathway inhibitor and CKI-7 (SIGMA) (final concentration 3 µM) as Wnt signal transduction pathway inhibitor (FIG. 17, NODALi+WNTi), the basal medium added with 10% KSR, Y-27632 (final concentration 10 µM), SB-431542 (final concentration 5 µM) (FIG. 17, NODALi), or the basal medium added with 10% KSR, Y-27632 (final concentration 10 µM) and CKI-7 (final concentration 3 µM) (FIG. 17, WNTi) was used. From 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-27 supplement (Life Technologies), 1.9 mM L-glutamine, 96 U/ml penicillin-96 µg/ml streptomycin] was used. The whole amount of the medium was exchanged every day.

Figure 17:
FIG. 17 shows photographs of 12-well culture plates after 43 days of culture containing iPS cell (QHJI01)-derived retinal pigment epithelial (RPE) cells produced by culture in the presence of a Nodal signal transduction pathway inhibitor and/or a Wnt signal transduction pathway inhibitor in the second step after the first step using "StemFit®" AK03N medium containing an MEK inhibitor (NODALi+WNTi, NODALi or WNTi). Differentiation-inducing effects of exposure to a Nodal signal transduction pathway inhibitor or a Wnt signal transduction pathway inhibitor alone in the second step were examined. NODALi: Nodal signal transduction pathway inhibitor (5 µM SB431542), WNTi: Wnt signal transduction pathway inhibitor (3 µM CKI-7).
Figure 17:
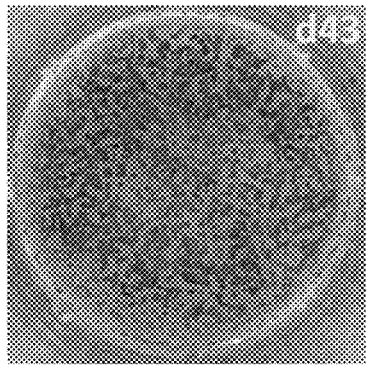
Figure 17:
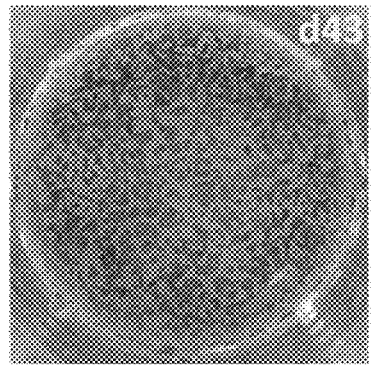
Figure 17:
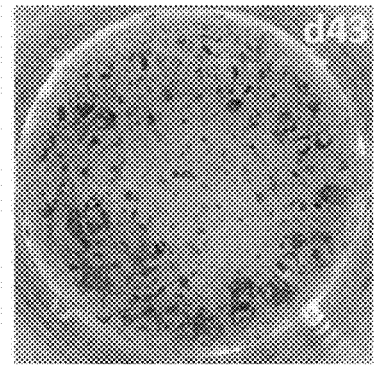

The culture plate was observed on day 43 of culture. As a result, emergence of cells showing the same level of typical characteristics of RPE cell such as a brown-black, polygonal, cobblestone-like morphology could be confirmed under both treatment conditions of Nodal signal transduction pathway inhibitor and Wnt signal transduction pathway inhibitor (NODALi+WNTi) and single agent treatment conditions of Nodal signal transduction pathway inhibitor (NODALi) was confirmed (FIG. 17, NODALi+WNTi, NODALi). By a single agent treatment of Wnt signal transduction pathway inhibitor (WNTi), the brown-black area in the whole well decreased; however, emergence of a sufficient number of cells showing the typical characteristics of RPE cell could be confirmed (FIG. 17, WNTi). From the above results, it could be confirmed that the presence of either Nodal signal transduction pathway inhibitor or Wnt signal transduction pathway inhibitor in the second step is sufficient.

Example 13: Relationship Between Area Ratio of Brown-Black Cell in Whole Well and Expression of Retinal Pigment Epithelial Cell Marker Gene Culture for maintaining undifferentiated state of human iPS cells (201B7 line) under feeder-free conditions was performed according to the method described in "Nakagawa, M. et. al., Sci. Rep. 2014 Jan. 8; 4: 3594". The medium used was "StemFit®" AK03 medium (Ajinomoto Co., Inc.) (hereinafter AK03 medium).

Production of retinal pigment epithelial (RPE) cells including an MEK inhibitor and BMP receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS (−)), dissociated using a cell scraper, dispersed to single cells by pipetting, seeded in a 6-well culture plate coated with iMatrix-511 (Nippi) (0.5 µg/cm$^2$) at 1.2×10$^4$ cells per 1 well and cultured in a ROCK inhibitor [10 µM Y-27632 (Wako Pure Chemical Industries, Ltd.)]-containing AK03 medium under 37° C., 5% $CO_2$ conditions. When the MEK inhibitor was to be exposed for 6 days and the BMP receptor inhibitor was to be exposed for 1 day, PD0325901 (SIGMA) (final concentration 1 µM) as an MEK inhibitor was added to the AK03 medium on the next day of seeding (start of the first step), and LDN193189 (STEMGENT) (final concentration 100 nM) as a BMP receptor inhibitor was added to the AK03 medium 6 days after the seeding, whereby the cells were exposed to the MEK inhibitor and the BMP receptor inhibitor for 6 days and 1 day, respectively (completion of the first step). When both the MEK inhibitor and the BMP receptor inhibitor were to be exposed for 6 days, PD0325901 (final concentration 1 µM) and LDN193189 (final concentration 100 nM) were added to the AK03 medium the next day of seeding (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 µg/cm$^2$) at 2.0×10$^5$ cells per 1 well and cultured under 37° C., 5% $CO_2$ conditions (start of the second step). On day 1 of culture, AK03 medium added with Y-27632 (final concentration 10 µM), SB-431542 (Wako Pure Chemical Industries, Ltd.) (final concentration 5 µM) as Nodal signal transduction pathway inhibitor, and CKI-7 (SIGMA) (final concentration 3 µM) was used; from 2 to 5 days of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 µg/ml streptomycin (Life Technologies)] added with 20% KSR (Life Technologies), Y-27632 (final concentration µM), SB-431542 (final concentration 5 µM) and CKI-7(final concentration 3 µM) was used; from 6 to 9 days of culture, the basal medium added with 15% KSR, Y-27632 (final concentration µM), SB-431542 (final concentration 5 µM), CKI-7 (final concentration 3 µM) was used; from 10 to 13 days of culture, the basal medium added with 10% KSR, Y-27632 (final concentration 10 µM), SB-431542 (final concentration 5 µM), CKI-7 (final concentration 3 µM) was used; from 14 to 30 days of culture, a basal medium added with 10% KSR alone was used; and from 31 days and thereafter of culture, RPE maintenance medium [67% DMEM low glucose (SIGMA), 29% F12 (SIGMA), 1.9% B-supplement (Life Technologies), 1.9 mM L-glutamine, 96 U/ml penicillin-96 µg/ml streptomycin] was used. The whole amount of the medium was exchanged every day. Simultaneously, RPE cells were also produced under the conditions of Comparative Example 1 not containing an MEK inhibitor treatment step.

After observation on day 39 of culture, the cells were collected, RNA was extracted and real-time RT-PCR was performed. RNeasy Mini Kit (QIAGEN) was used for RNA extraction and QuantiTect Probe RT-PCR Kit (QIAGEN) was used for real-time RT-PCR. The primers and probes for BEST1 (Hs00188249_m1), MITF (Hs01117294_m1), RAX (Hs00429459_m1), GAPDH (Hs02758991_g1) were purchased from Applied Biosystems. The expression levels of BEST1, MITF and RAX of each sample were normalized by the expression level of GAPDH and represented as a relative value to the expression level of iPS cells (undifferentiated) cultured under conditions for maintaining undifferentiated state as 1.

Figure 18:
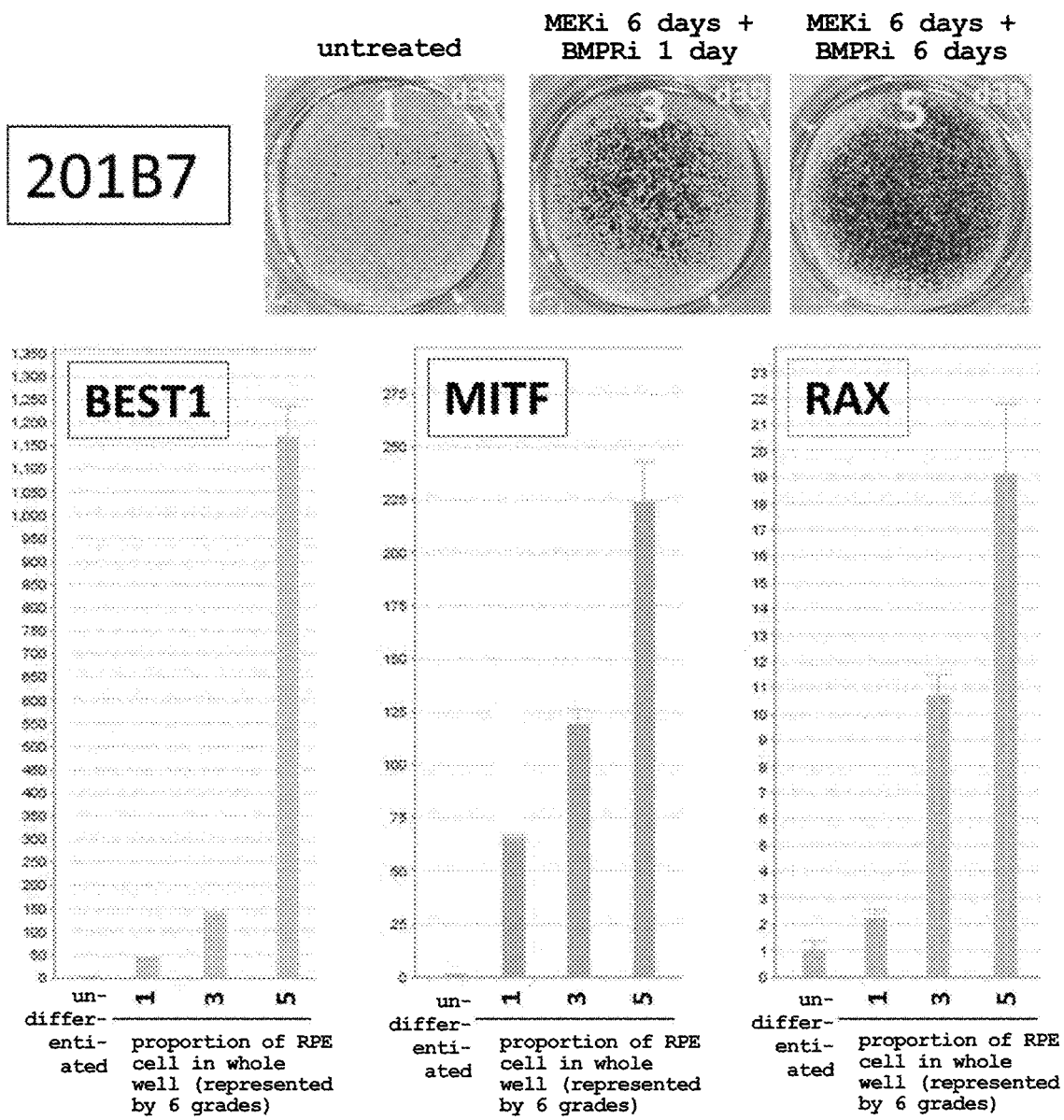
FIG. 18 shows percentages of iPS cell (201B7)-derived retinal pigment epithelial (RPE) cells, which were produced by a production method comprising an MEK inhibitor and BMP receptor inhibitor treatment step using "StemFit®" AK03N medium, in a whole well after 39 days of culture, which percentages are results by visual judgment according to FIG. 8A (upper in the figure, MEKi for 6 days+BMPRi for 1 day or MEKi for 6 days+BMPRi for 6 days), and results of comparison of the expression levels of retinal pigment epithelium markers, BEST1 and MITF, and a marker in the early stage of eye formation, RAX, after 39 days of culture by a real-time RT-PCR method (lower in the figure, percentage of RPE cells in a whole well ("3" and "5" of a 6-point scale)). For comparison, results of visual judgment of percentages of RPE cells in a whole well of iPS cell-derived differentiated cells produced by a production method without an MEK inhibitor and/or BMP receptor inhibitor treatment step after 39 days of culture (upper in the figure, "untreated"), and expression levels of BEST1, MITF and RAX (lower in the figure, percentage of RPE cells in a whole well ("1" of a 6-point scale)) are also shown. The gene expression level in each sample was normalized by the expression level of GAPDH, and shown as a relative amount when the expression level in iPS cells cultured under conditions for maintaining undifferentiated state is defined as 1 for comparison of BEST1, MITF or RAX expression levels (lower in the figure, "undifferentiated").

Based on the observed images of culture plates on day 39 of culture and according to FIG. 8A, the proportion of RPE cells in the whole well was determined by visual observation. As a result, untreated condition was "1", MEK inhibitor 6 days+BMP receptor inhibitor 1 day exposure was "3", and MEK inhibitor 6 days+BMP receptor inhibitor 6 days exposure was "5" (FIG. 18, upper side, cell photograph). The expression levels of BEST1, MITF as retinal pigment epithelial cell markers and RAX as a marker of early eye formation stage were compared by a real time RT-PCR method between these samples and the sample of iPS cells (undifferentiated) under continuous culturing for maintaining undifferentiated state. As a result, a correlation was found between the area of brown-black cells and the expression levels of the marker genes described above (FIG. 18, lower side, graph). From the above results, it was suggested that brown-black cells express retinal pigment epithelial cell marker gene and marker gene of early eye formation stage. In addition, production of RPE cells by this production method was also verified by checking these gene expression levels.

Example 14: Confirmation of Expression of Marker Gene of RPE Cell Produced by Production Method Including MEK Inhibitor or FGF Receptor Inhibitor Treatment Step Culture for maintaining undifferentiated state of human iPS cells (1231A3 line) under feeder-free conditions was performed according to the method described in "Nakagawa, M. et. al., Sci. Rep. 2014 Jan. 8; 4: 3594". The medium used was "StemFit®" AK03N medium (Ajinomoto Co., Inc.) (hereinafter AK03N medium).

Production of retinal pigment epithelial (RPE) cells including an MEK inhibitor or FGF receptor inhibitor treatment step was performed as follows. iPS cells under culture for maintaining undifferentiated state were treated with 0.5×TrypLE select (mixture of equal amounts of TrypLE select (Life Technologies) and 0.5 mM EDTA/PBS(−)), dissociated using a cell scraper, dispersed to single cells by pipetting, seeded in a 6-well culture plate coated with iMatrix-511 (Nippi) (0.5 μg/cm$^2$) at $2.0 \times 10^4$ cells per 1 well and cultured in a ROCK inhibitor [10 μM Y-27632 (Wako Pure Chemical Industries, Ltd.)]-containing AK03N medium under 37° C., 5% CO$_2$ conditions. On the next day of seeding, PD0325901 (SIGMA) (final concentration 1 μM) as MEK inhibitor or PD173074 (SIGMA) (final concentration nM) as FGF receptor inhibitor was added to the AK03N medium (start of the first step) and the cells were exposed thereto for 6 days (completion of the first step). Thereafter, the cells were treated with 0.5×TrypLE select, dissociated using a cell scraper, dispersed to single cells by pipetting, seeded in a 6-well culture plate coated with iMatrix-511 (0.5 μg/cm$^2$) at $2.0 \times 10^5$ cells per 1 well and cultured under 37° C., 5% CO$_2$ conditions (start of the second step). From day 1 to day 4 of culture, a basal medium [GMEM medium (SIGMA), 0.1 mM MEM non-essential amino acid solution (Life Technologies), 1 mM sodium pyruvate (SIGMA), 0.1 mM 2-mercaptoethanol (Wako Pure Chemical Industries, Ltd.), 2 mM L-glutamine (SIGMA), 100 U/ml penicillin-100 μg/ml streptomycin (Life Technologies)] added with 20% KSR (Life Technologies), Y-27632 (final concentration μM), SB-431542 (Wako Pure Chemical Industries, Ltd.) (final concentration 5 μM) as Nodal signal transduction pathway inhibitor and CKI-7 (SIGMA) (final concentration 3 μM) as Wnt signal transduction pathway inhibitor was used; from 5 to 8 days of culture, the basal medium added with 15% KSR, Y-27632 (final concentration 10 μM), SB-431542 (final concentration 5 μM) and CKI-7 (final concentration 3 μM) was used; from 9 to 12 days of culture, the basal medium added with 10% KSR, Y-27632 (final concentration 10 μM), SB-431542 (final concentration 5 μM) and CKI-7 (final concentration 3 μM); from 13 to 30 days of culture, the basal medium added with 10% KSR alone was used; and from 31 days and thereafter of culture, RPE maintenance medium [67% DMEM low glucose (SIGMA), 29% F12 (SIGMA), 1.9% B-supplement (Life Technologies), 1.9 mM L-glutamine, 96 U/ml penicillin-96 μg/ml streptomycin] was used. The whole amount of the medium was exchanged every day. Simultaneously, the experiment was also performed under the conditions of Comparative Example 1 not containing an MEK inhibitor treatment step (AK03 medium was changed to AK03N medium).

After observation on day 43 of culture, the cells were collected, RNA was extracted and RT-PCR was performed. RNeasy Micro Kit (QIAGEN) was used for RNA extraction, Oligo(dT)$_{12-18}$ Primer (Invitrogen) and SuperScript III Reverse Transcriptase (Invitrogen) were used for reverse transcription reaction, and Blend Taq-Plus-(TOYOBO) was used for PCR. The primer sequences of RPE65, BEST1, CRALBP, GAPDH are as described below.

```
                                          (SEQ ID NO: 1)
          RPE65-F: TCCCCAATACAACTGCCACT, (SEQ ID NO: 2)
          RPE65-R: CCTTGGCATTCAGAATCAGG, (SEQ ID NO: 3)
          BEST1-F: TAGAACCATCAGCGCCGTC, (SEQ ID NO: 4)
          BEST1-R: TGAGTGTAGTGTGTATGTTGG, (SEQ ID NO: 5)
          CRALBP-F: GAGGGTGCAAGAGAAGGACA, (SEQ ID NO: 6)
          CRALBP-R: TGCAGAAGCCATTGATTTGA, (SEQ ID NO: 7)
          GAPDH-F: ACCACAGTCCATGCCATCAC, (SEQ ID NO: 8)
          GAPDH-R: TCCACCACCCTGTTGCTGTA.
```

The number of cycles of the PCR reaction was 30 cycles for RPE65, BEST1, GAPDH, and 35 cycles for CRALBP. PCR products were detected as a single band by agarose gel electrophoresis at near 369 bp for RPE65, near 261 bp for BEST1, near 341 bp for CRALBP, and near 452 bp for GAPDH. As a positive control, primary human RPE (hRPE) was used and, as a negative control, iPS cells (undifferentiated iPSC) cultured under conditions for maintaining undifferentiated state were used.

Figure 19:
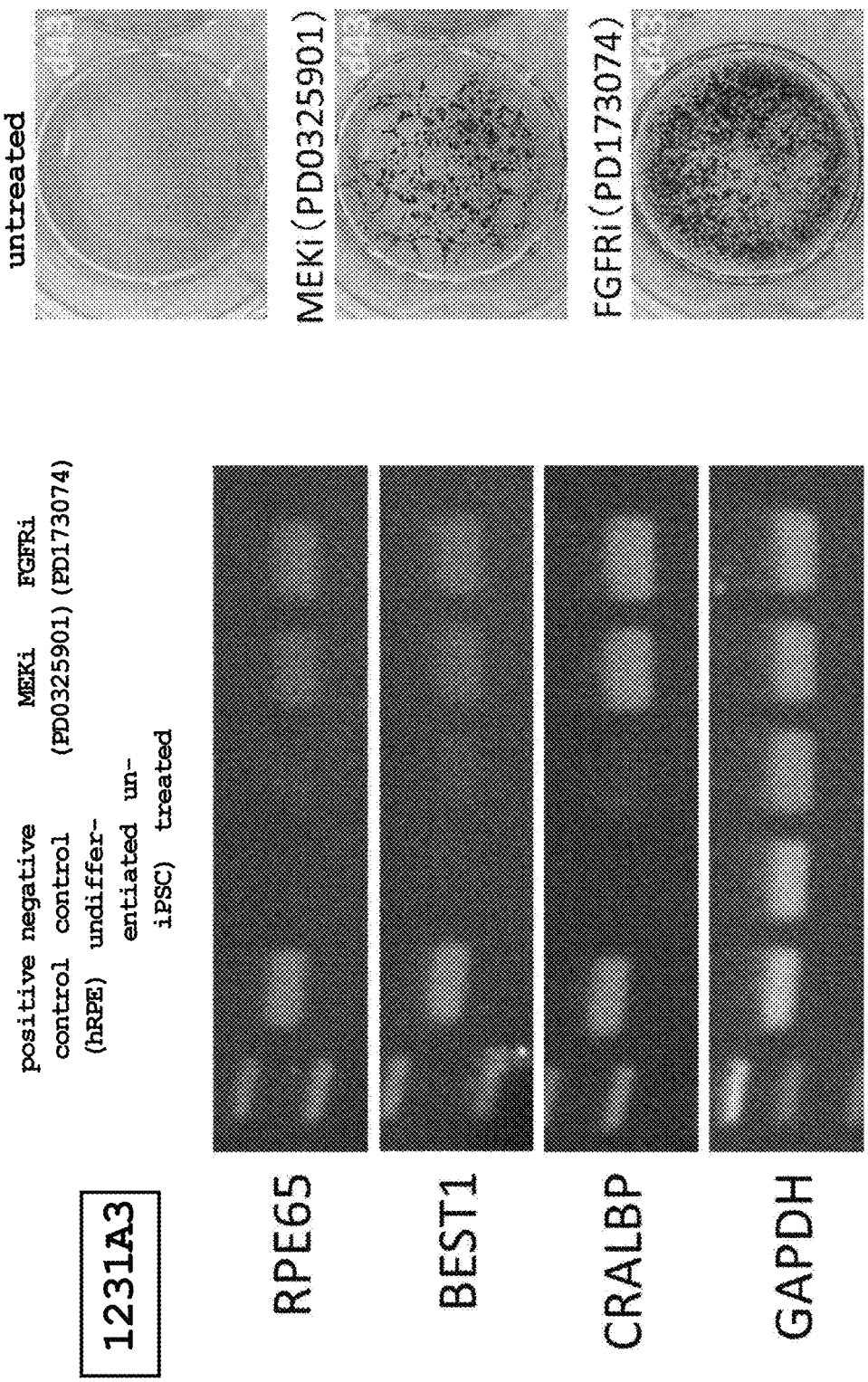
FIG. 19 shows photographs of 6-well culture plates after 43 days of culture containing iPS cell (1231A3)-derived retinal pigment epithelial (RPE) cells produced by a production method comprising an MEK inhibitor or FGF receptor inhibitor treatment step using "StemFit®" AK03N medium (right in the figure, MEKi (PD0325901), FGFRi (PD173074)), and results of confirmation of the expression of retinal pigment epithelium markers RPE65, BEST1 and CRALBP, and an endogenous control GAPDH after 43 days of culture by RT-PCR method (left in the figure, MEKi (PD0325901), FGFRi(PD173074)). For comparison, photographs of 6-well culture plates after 43 days of culture containing iPS cell-derived differentiated cells produced by a production method without an MEK inhibitor and/or FGF receptor inhibitor treatment step (right in the figure, untreated), and results of RT-PCR for RPE65, BEST1, CRALBP and GAPDH are also shown (left in the figure, untreated). A primary human RPE was used as a positive control (left in the figure, hRPE), and iPS cells cultured under conditions for maintaining undifferentiated state were used as a negative control (left in the figure, undifferentiated iPSC) for the RT-PCR method.

The culture plate was observed on day 43 of culture. As a result, only a few cells could be confirmed to show typical characteristics of RPE cell such as a brown-black, polygonal, cobblestone-like morphology under the conditions of Comparative Example 1 (FIG. 19, right side, cell photograph, untreated). On the other hand, when exposed to MEK inhibitor and FGF receptor inhibitor, emergence of a brown-black cell population could be confirmed over a wide area (FIG. 19, right side, cell photograph, MEKi, FGFRi). As a result of RT-PCR, the bands of retinal pigment epithelial cell markers RPE65, BEST1, CRALBP were very thin under the conditions of Comparative Example 1 (FIG. 19, left side, electrophoretic pattern, untreated). On the other hand, clear bands could be confirmed in the samples exposed to the MEK inhibitor and FGF receptor inhibitor (FIG. 19, left side, electrophoretic pattern, MEKi, FGFRi). From the above results, highly efficient production of RPE cells by the production method including an MEK inhibitor and FGF receptor inhibitor treatment step was also verified by checking these gene expression levels.

INDUSTRIAL APPLICABILITY

The production method of the present invention enables highly efficient production of retinal pigment epithelial cells from pluripotent stem cells.

This application is based on a patent application No. 2015-176896 filed in Japan (filing date: Sep. 8, 2015), the contents of which are incorporated in full herein.

The invention claimed is:

1. A production method of a human retinal pigment epithelial cell comprising the following steps:
   (1) a maintenance and/or expanding step of maintaining and/or expanding human pluripotent stem cells comprising culturing the human pluripotent stem cells in the absence of a feeder cell in a medium comprising a factor for maintaining an undifferentiated state,
   (2) a first step for culturing the maintained and/or expanded human pluripotent stem cells in a medium comprising an FGF receptor inhibitor in the absence of feeder cells for a period of not less than 2 days and not more than 30 days, wherein the culture condition in the first step is a condition sufficient for inducing gene expression of at least one eye field transcription factor, wherein the first step excludes the presence of a MEK inhibitor, and
   (3) a second step for culturing the cells obtained in the first step in the presence of a Nodal signal transduction pathway inhibitor and/or a Wnt signal transduction pathway inhibitor to form a retinal pigment epithelial cell.

2. The production method according to claim 1, wherein the first step is performed in serum-free conditions.

3. The production method according to claim 1, wherein the maintenance and/or expanding step, the first step, and/or the second step is performed under adherent conditions.

4. The production method according to claim 1, wherein the medium in the first step further comprises a factor for maintaining undifferentiated state.

5. The production method according to claim 4, wherein the factor for maintaining undifferentiated state is an FGF signal transduction pathway agonist.

6. The production method according to claim 5, wherein the FGF signal transduction pathway agonist is bFGF.

7. The production method according to claim 1, wherein the FGF receptor inhibitor is at least one kind selected from the group consisting of PD173074 and SU5402.

8. The production method according claim 1, wherein the Nodal signal transduction pathway inhibitor is an Alk4, 5 or 7 inhibitor.

9. The production method according to claim 8, wherein the ALK4, 5 or 7 inhibitor is SB431542.

10. The production method according to claim 1, wherein the Wnt signal transduction pathway inhibitor is CKI-7.

11. The production method according to claim 1, wherein the medium in the first step is a medium further comprising a BMP receptor inhibitor.

12. The production method according to claim 11, wherein the BMP receptor inhibitor is an ALK2/3 inhibitor.

13. The production method according to claim 12, wherein the ALK2/3 inhibitor is LDN193189.

14. The production method according to claim 1, wherein the medium in the first step further comprises a Sonic hedgehog signal transduction pathway agonist.

15. The production method according to claim 14, wherein the Sonic hedgehog signal transduction pathway agonist is SAG.

16. The production method according to claim 1, wherein the medium in the first step further comprises a PKC inhibitor.

17. The production method according to claim 16, wherein the PKC inhibitor is Go6983.

18. The production method according to claim 1, wherein the culture period in the first step is for 2 days to 13 days.

19. The production method according to claim 1, wherein the culture period in the first step is for 4 days to 6 days.

20. A method of evaluating toxicity or efficacy of a test substance comprising contacting a retinal pigment epithelial cell produced by the production method according to claim 1 with the substance, and assaying the effect of the substance on the cells.

21. The production method according to claim 1, wherein the culture period in the first step is a period sufficient for inducing gene expression of at least one of PAX6, LHX2, and SIX3.

22. The production method according to claim 1, wherein the first step further excludes the presence of a ROCK inhibitor.

23. The production method according to claim 1, wherein the factor for maintaining undifferentiated state is an FGF signal transduction pathway agonist.

24. The production method according to claim 23, wherein the FGF signal transduction pathway agonist is bFGF.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic Forward primer for RPE65

<400> SEQUENCE: 1
tccccaatac aactgccact                                                  20

<210> SEQ ID NO 2
<211> LENGTH: 20
<212> TYPE: DNA
<213> ORGANISM: Artificial Sequence
<220> FEATURE:
<223> OTHER INFORMATION: Synthetic Reverse primer for RPE65

<400> SEQUENCE: 2
ccttggcatt cagaatcagg                                                  20

<210> SEQ ID NO 3
<211> LENGTH: 19
<212> TYPE: DNA
<213> ORGANISM: Artificial Sequence
<220> FEATURE:
<223> OTHER INFORMATION: Synthetic Forward primer for BEST1

<400> SEQUENCE: 3
tagaaccatc agcgccgtc                                                   19

<210> SEQ ID NO 4
<211> LENGTH: 21
<212> TYPE: DNA
<213> ORGANISM: Artificial Sequence
<220> FEATURE:
<223> OTHER INFORMATION: Synthetic Reverse primer for BEST1

<400> SEQUENCE: 4
tgagtgtagt gtgtatgttg g                                                21

<210> SEQ ID NO 5
<211> LENGTH: 20
<212> TYPE: DNA
<213> ORGANISM: Artificial Sequence
<220> FEATURE:
<223> OTHER INFORMATION: Synthetic Forward primer for CRALBP

<400> SEQUENCE: 5
gagggtgcaa gagaaggaca                                                  20

<210> SEQ ID NO 6
```

```
<211> LENGTH: 20
<212> TYPE: DNA
<213> ORGANISM: Artificial Sequence
<220> FEATURE:
<223> OTHER INFORMATION: Synthetic Reverse primer for CRALBP

<400> SEQUENCE: 6
tgcagaagcc attgatttga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Forward primer for GAPDH

<400> SEQUENCE: 7
accacagtcc atgccatcac                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Reverse primer for GAPDH

<400> SEQUENCE: 8
tccaccaccc tgttgctgta                                              20
```